United States Patent
Pendse et al.

(10) Patent No.: US 9,489,346 B1
(45) Date of Patent: Nov. 8, 2016

(54) METHODS AND SYSTEMS FOR EARLY STOP SIMULATED LIKELIHOOD RATIO TEST

(71) Applicants: Gautam Pendse, Hopkinton, MA (US); Thomas Lane, Carlisle, MA (US)

(72) Inventors: Gautam Pendse, Hopkinton, MA (US); Thomas Lane, Carlisle, MA (US)

(73) Assignee: The Mathworks, Inc., Natick, MA (US)

( * ) Notice: Subject to any disclaimer, the term of this patent is extended or adjusted under 35 U.S.C. 154(b) by 353 days.

(21) Appl. No.: 13/804,631

(22) Filed: Mar. 14, 2013

(51) Int. Cl.
*G06F 17/18* (2006.01)
*G06K 9/62* (2006.01)

(52) U.S. Cl.
CPC ............. *G06F 17/18* (2013.01); *G06K 9/6277* (2013.01)

(58) Field of Classification Search
None
See application file for complete search history.

(56) References Cited

U.S. PATENT DOCUMENTS

| | | | |
|---|---|---|---|
| 7,085,690 B2 * | 8/2006 | Sale | 703/2 |
| 7,474,997 B2 * | 1/2009 | Acharya | 703/2 |
| 8,478,534 B2 * | 7/2013 | Zhu | G06F 17/18 702/19 |
| 2004/0236776 A1 * | 11/2004 | Peace | 707/100 |
| 2012/0323834 A1 * | 12/2012 | Fujimaki | 706/46 |
| 2014/0258355 A1 * | 9/2014 | Chu et al. | 708/446 |
| 2015/0006605 A1 * | 1/2015 | Chu et al. | 708/446 |

OTHER PUBLICATIONS

Wood, Simon N. "Fast stable Restricted Maximum Likelihood and Marginal Likelihood Estimation of Semiparametric Generalized Linear Models" J. Royal Statistical Society, Series B (Statistical Methodology), vol. 73, No. 1, pp. 3-36 (2011).*
Feng, Z.D. & McCulloch, C.E. "Using Bootstrap Likelihood Ratio in Finite Mixture Models" J. Royal Statistical Society, Series B (Methodological), vol. 58, No. 3. pp. 609-617 (1996) available at <https://dspace.library.cornell.edu/bitstream/1813/31856/1/BU-1268-M.pdf>.*
Wood, Simon N. "Fast Stable Direct Fitting and Smoothness Selection for Generalized Additive Models" J. Royal Statistical Society, Series B, vol. 70, pp. 495-518 (2008).*
Gurka, Matthew "Selecting the Best Linear Mixed Model Under REML" American Statistical Association, vol. 60, No. 1, pp. 19-26 (2006).*
Tutz, Gerhard & Binder, Harald "Generalized additive modelling with implicit variable selection by likelihood based boosting" (2004).*

(Continued)

*Primary Examiner* — Kamini S Shah
*Assistant Examiner* — Jay B Hann
(74) *Attorney, Agent, or Firm* — Finnegan, Henderson, Farabow, Garrett & Dunner, LLP

(57) ABSTRACT

A method for modeling a set of observed data comprises selecting a reference model and an alternative model as possible descriptions of the set of observed data, and storing an index function for measuring fit of models to data. The method further includes performing, by one or more processors, a simulated threshold-fitting for a first of the two models, deriving an initial simulated index for the second model for fitting the second model to the simulated data, and deriving an initial boundary for simulated index difference including calculating a difference between the threshold-fit simulated index for the first model and the initial simulated index for the second model. The method further includes determining, based on a comparison, whether to update a counter used in calculating a simulated p-value, and selecting, based on the simulated p-value, one of the reference and alternative models for modeling the set of observed data.

22 Claims, 12 Drawing Sheets

(56) References Cited

OTHER PUBLICATIONS

Nylund, Karen L., et al. "Deciding on the Number of Classes in Latent Class Analysis and Growth Mixture Modeling: A Monte Carlo Simulation Study" Structural Equation Modeling, vol. 14, No. 4, pp. 535-569 (2007).*

Tekle, Fetene, et al. "Power analysis for the Bootstrap Likelihood Ratio Test in Latent Class Models" <http://members.home.nl/jeroenvermunt/tekle2013.pdf> (Oct. 2013).*

McLachlan, Geoffrey & Peel, David "Finite Mixture Models" (2000) (Chapter 6: Assessing the Number of Components in Mixture Models).*

Dempster, et al. "Maximum Likelihood from Incomplete Data via the EM Algorithm" J. Royal Statistical Society, Series B (Methodological), vol. 39, No. 1, pp. 1-38 (1977).*

Yang, Chih-Chien "Separating Latent Classes by Information Criteria" J. Classification, vol. 24, pp. 183-203 (2007).*

Lai, Tze Leung "On Optimal Stopping Problems in Sequential Hypothesis Testing" Statistica Sinica, vol. 7, pp. 33-51 (1997).*

Shih, Mei-Chiung, et al. "Sequential Generalized Likelihood Ratio Tests for Vaccine Safety Evaluation" Stat. Med., vol. 29, pp. 2698-2708 (2010) available from <http://statweb.stanford.edu/~ckirby/lai/pubs/2010_SequentialGLR.pdf>.*

Kulldorff, Martin, et al. "A Maximized Sequential Probability Ratio Test for Drug and Vaccine Safety Surveillance" Sequential Analysis, vol. 30, pp. 58-78 (2011).*

Chernoff et al., "On the Distribution of the Likelihood Ratio," Ann Math Statistics, vol. 25 (3), pp. 573-578 (1954).

Clopper et al., "The Use of Confidence or Fiducial Limits Illustrated in the Case of the Binomial," Biometrika Trust, vol. 26 (4), pp. 404-413 (1934).

Langford et al.,"Tutorial on Practical Prediction Theory for Classification" J Machine Learn Res, vol. 6, pp. 273-306 (2005).

Self et al., "Asymptotic Properties of Maximum Likelihood Estimators and Likelihood Ratio Tests Under Nonstandard Conditions," J Am Statistical Assoc, vol. 82 (398), pp. 605-610 (1987).

Wang,"Fiducial Intervals: What are They?" Am Statistician, vol. 54 (2), pp. 105-111 (2000).

Wilks,"The Large-Sample Distribution of the Likelihood Ratio for Testing Composite Hypotheses" Ann Math Statistics, vol. 9 (1), pp. 60-62 (1938).

* cited by examiner

METHODS AND SYSTEMS FOR EARLY STOP SIMULATED LIKELIHOOD RATIO TEST

TECHNICAL FIELD

The present disclosure relates generally to methods and systems for comparing parametric statistical models and in particular to likelihood ratio tests.

BACKGROUND

Empirical studies in many fields of science and technology collect a set of data and use the data to examine a theoretical model related to that field. Such empirical studies apply in a variety of areas, such as healthcare, drug development, finance, or stock market modeling and predictions.

In one example, a cancer drug development group identifies a family of drugs as candidates for inhibiting the growth of cancerous tumor cells. The drugs can be administered in one of three candidate carrier solutions. The group wants to identify an effective drug and a corresponding suitable family of carrier solutions. To that end, the group compares the drugs, two at a time, by performing a bioassay experiment on multiple equivalent tumor cells placed in multiple isolated slots of a bioassay plate. The group treats randomly selected subsets of the slots with each of the two drugs administered in one of the three carrier solutions. After a period of time, the cells are examined to determine the number of tumor cells that are alive in each slot. The effectiveness of each drug is measured by the number of cells that are killed during the time period. The group would like to determine whether there exists any variability in the effectiveness of drugs across the drug family, in the effectiveness of carrier solutions across the carrier family, and in the interactions between different drug and carrier solution combinations.

In another example, a clinical trial group studies a newly developed antihypertensive drug for lowering blood pressure in humans. To that end, the clinical trial selects a group of patients with a history of hypertension. Each patient visits the clinic five times. During each visit, the patient randomly receives one of the five options: a placebo and four different doses of the drug. The clinical trial monitors the blood pressure and other health parameters of each patient during the study. Based on the results, the scientists would like to determine the effectiveness of the drug and, if effective, a proper dose of the drug.

Many of these studies apply statistical modeling to solve the problem. In statistical modeling, researchers often attempt to describe the observed data with a model. In many cases the researchers know of multiple candidate models that may describe the data and want to find from among those candidates a model that describes the data in a best manner. In many cases, a candidate model is a parametric model, which includes some variable parameters.

For example, the cancer drug development example above may use a 2-way completely randomized analysis of variance (ANOVA) with interactions model. In this parametric model, the measured data are explained by equation (1):

$$y_{ijk} = \mu + \alpha_i + b_j + c_{ij} + \epsilon_{ijk} \tag{1}$$

In equation (1), the index i runs over the values 1, and 2 for the two drugs; the index j runs over the values 1, 2, and 3 for the three carrier solutions; and the index k runs over the number of measurements. Further, the parameters and values are defined as follows:

$y_{ijk}$ = kth measurement of response after treatment with drug i in carrier solution j
$\mu$ = mean response
$\alpha_i \sim N(0, \sigma_a^2)$ = contribution of drug i to $y_{ijk}$
$b_j \sim N(0, \sigma_b^2)$ = contribution of carrier j to $y_{ijk}$
$c_{ij} \sim N(0, \sigma_c^2)$ = contribution of (drug i, carrier j) interaction to $y_{ijk}$
$\epsilon_{ijk} \sim N(0, \sigma^2)$ = contribution of error term to $y_{ijk}$ Moreover, the parameters $\alpha_i$, $b_j$, $c_{ij}$ and $\epsilon_{ijk}$ are independent of each other.

The clinical trial example above, on the other hand, may use a the quadratic model shown in equation (2):

$$y_{ij} = \alpha_i + \beta_i I_{ij} + \gamma_i I_{ij}^2 + \epsilon_{ij} \tag{2}$$

In equation (2), the index i runs over the number of patients and the index j runs over 1 to 5 for the five visits. Further, the parameters and values are defined as follows:

$y_{ij}$ = reduction in blood pressure on the jth visit for subject i
$I_{ij}$ = concentration of drug administered to subject I on the jth visit ($I_{ij}=0$ for placebo)
$\alpha_i$ = subject specific intercept
$\beta_i$ = subject specific slope
$\gamma_i$ = subject specific quadratic coefficient
$\epsilon_{ij} \sim N(0, \sigma^2)$ = error term which is independent for different i or j In one example, the subject specific parameters above may be derived from the population level values as $\alpha_i = \alpha + a_i$; $\beta_i = \beta + b_i$; and $\gamma_i = \gamma + c_i$ in which $\alpha$ is population level intercept, $\beta$ is population level slope, and $\gamma$ is population level quadratic coefficient. Moreover, $$\begin{pmatrix} a_i \\ b_i \\ c_i \end{pmatrix} \sim N(0, \sigma^2 D)$$

where D is a symmetric positive semi-definite matrix, and $(a_i, b_i, c_i)^T$ is independent for various i and also independent of $\epsilon_{ij}$ in equation (2).

Substituting the above values in equation (2) results in the model shown in equation (3):

$$y_{ij} = (\alpha + a_i) + (\beta + b_i) I_{ij} + (\gamma + c_i) + \epsilon_{ij} \tag{3}$$

In some studies, a researcher may propose different models. A first model is said to be nested in a second model if the first model can be derived from the second model by imposing constraints on the parameters of the second model. Is some embodiments, a researcher chooses between a base model and an alternative model. The base model can be more complex or less complex than the alternative model. In some embodiments, the base model is nested in the alternative model. In some other embodiments, the alternative model is nested in the base model. Further, in some embodiments, none of the base model and the alternative model is nested in the other model.

For instance, in the first example, a researcher may hypothesize that one or more of the parameters $a_i$, $b_j$, or $c_{ij}$, are not needed and thus can be set to zero. Similarly, in the second example, a researcher may define a reduced model for the clinical trial study by hypothesizing that the population average of $\gamma_j$ is not needed in the model. The researcher may desire to compare these alternative reduced models with each other and with the full model of Equation (1) or Equation (2). In particular, the researcher may desire to compare the models for their accuracy in explaining the data.

SUMMARY

In some embodiments, a method for modeling a set of observed data comprises selecting a reference model as a possible description of the set of observed data, wherein the reference model includes a reference set of parameters; selecting an alternative model as another possible description of the set of observed data, wherein the alternative model includes an alternative set of parameters; storing an index function for measuring fit of models to data; calculating an observed index difference based on a difference in the index function for fitting the reference model to the observed data and for fitting the alternative model to the data; generating a set of simulated data; selecting a first model and a second model, wherein the first model is one of the reference model and the alternative model and the second model is the other one of the reference model and the alternative model; performing, by one or more processors, an operation based on the set of simulated data, wherein the operation includes performing a simulated threshold-fitting for the first model by the one or more processors, wherein the simulated threshold-fitting for the first model includes varying the set of parameters for the first model for fitting the first model to the simulated data and deriving a threshold-fit simulated index for the first model as a value of the index function for the first model that satisfies a threshold criterion; deriving an initial simulated index for the second model as an initial value of the index function for fitting the second model to the simulated data; and deriving an initial boundary for simulated index difference, wherein deriving the initial boundary for simulated index difference includes calculating a difference between the threshold-fit simulated index for the first model and the initial simulated index for the second model; determining, based on a comparison of the initial boundary for simulated index difference and the observed index difference, whether to update a counter used in calculating a simulated p-value; and selecting, based on the simulated p-value, one of the reference model and the alternative model for modeling the set of observed data.

In some embodiments, the first simulated threshold-fitting includes a first maximization, and the first maximization includes deriving the threshold-fit simulated index for the first model as a maximum simulated index for the first model by varying the set of parameters for the first model and maximizing the index function for fitting the first model to the simulated data.

In some embodiments, the method further comprises storing observed fit parameters for the reference model based on maximizing the index function for fitting the reference model to the observed data, and storing observed fit parameters for the alternative model based on maximizing the index function for fitting the alternative model to the observed data.

In some embodiments, deriving the initial simulated index for the second model includes setting the set of parameters for the second model to the observed fit parameters for the second model and deriving the index function for fitting the second model to the simulate data.

In some embodiments, the operation further comprises deriving an updated boundary for simulated index difference, wherein deriving the updated boundary for simulated index difference includes deriving an updated simulated index for the second model as an updated value of the index function for fitting the second model to the simulated data and calculating a difference between the threshold-fit simulated index for the first model and the updated simulated index for the second model; and wherein the method further comprises determining, based on a comparison of the updated boundary for simulated index difference and the observed index difference, whether to update the counter.

In some embodiments, deriving an updated simulated index for the second model includes deriving a maximum simulated index for the second model by a second maximization, and the second maximization includes varying the set of parameters for the second model and maximizing the index function for fitting the second model to the simulated data. In some embodiments, performing the simulated threshold-fitting for the first model deriving an updated simulated index for the second model are performed in parallel.

In some embodiments, the first model is the reference model and the second model is the alternative model, and the initial boundary for simulated index difference is an initial lower boundary for a simulated index difference, and the determining whether to update the counter includes increasing the counter if the initial lower boundary for the simulated index difference is larger than or equal to the observed index difference.

In some embodiments, the operation further comprises determining that the initial lower boundary for the simulated index difference is smaller than the observed index difference; and deriving an updated lower boundary for the simulated index difference, wherein deriving the updated lower boundary for the simulated index difference includes deriving an updated simulated index for the alternative model as an updated value of the index function for fitting the alternative model to the simulated data and subtracting the threshold-fit simulated index for the reference model from the updated simulated index for the alternative model; and wherein the method further comprises increasing the counter if the updated lower boundary for the simulated index difference is larger than or equal to the observed index difference.

In some embodiments, deriving an updated simulated index for the alternative model includes deriving a maximum simulated index for the alternative model via maximizing the index function for fitting the alternative model to the simulated data, deriving an updated lower boundary for the simulated index difference includes deriving the simulated index difference by subtracting the threshold-fit simulated index for the reference model from the maximum simulated index for the alternative model, and the method further comprises increasing the counter if the simulated index difference is larger than or equal to the observed index difference; and determining to leave the counter unchanged if the simulated index difference is smaller than the observed index difference.

In some embodiments, the first model is the alternative model and the second model is the reference model, and the initial boundary for simulated index difference is an initial upper boundary for a simulated index difference, and the determining whether to update the counter includes determining to leave the counter unchanged if the initial upper boundary for the simulated index difference is smaller than the observed index difference.

In some embodiments, the operation further comprises determining that the initial upper boundary for the simulated index difference is not smaller than the observed index difference; and deriving an updated upper boundary for the simulated index difference, wherein deriving the updated upper boundary for the simulated index difference includes deriving an updated simulated index for the reference model as an updated value of the index function for fitting the reference model to the simulated data and subtracting the updated simulated index for the reference model from the threshold-fit simulated index for the alternative model; and wherein the method further comprises determining to leave the counter unchanged if the updated upper boundary for the simulated index difference is smaller than the observed index difference.

In some embodiments, deriving an updated simulated index for the reference model includes deriving a maximum simulated index for the reference model via maximizing the index function for fitting the reference model to the simulated data, deriving an updated upper boundary for the simulated index difference includes deriving the simulated index difference by subtracting the maximum simulated index for the reference model from the threshold-fit simulated index for the alternative model, and the method further comprises increasing the counter if the simulated index difference is larger than or equal to the observed index difference; and determining to leave the counter unchanged if the simulated index difference is smaller than the observed index difference.

In some embodiments, the method further comprises a plurality of simulation iterations, wherein each iteration of the plurality of simulation iterations includes the generating a set of simulated data for the iteration and further includes, based on the set of simulated data for the iteration, the performing an operation based on the set of simulated data and the determining whether to update the counter In some embodiments, each iteration of the plurality of simulation iterations includes randomly deciding whether setting the first model to be the reference model or to be the alternative model. In some embodiments, each iteration of the plurality of simulation iterations includes deciding whether the first model is the reference model or the alternative model based on an outcome of one or more of the previous iterations of the plurality of simulation iterations. In some embodiments, each iteration further includes setting a weight value to 0.5 if the iteration is a first iteration of the plurality of simulation iterations; otherwise calculating the weight value as a ratio of previous iterations in which the counter was decided to be increased; and creating a random variable for which a probability of being one is the weight value; and setting the first model to be the reference model if the random variable is one, otherwise setting the first model to be the alternative model. In some embodiments, two iterations of the plurality of simulation iterations are performed in parallel. In some embodiments, the index function is a logarithm of a density function.

In some embodiments, a comparison system for modeling a set of observed data comprises an analyzer module configured to select a reference model as a possible description of the set of observed data, wherein the reference model includes a reference set of parameters, select an alternative model as another possible description of the set of observed data, wherein the alternative model includes an alternative set of parameters; store an index function for measuring fit of models to data; calculate an observed index difference based on a difference in the index function for fitting the reference model to the observed data and for fitting the alternative model to the data; and select a first model and a second model, wherein the first model is one of the reference model and the alternative model and the second model is the other one of the reference model and the alternative model; a simulator module configured to generate a set of simulated data; a first maximizer module configured to perform an operation based on the set of simulated data, wherein the operation includes performing a simulated threshold-fitting for the first model by the one or more processors, wherein the simulated threshold-fitting for the first model includes varying the set of parameters for the first model for fitting the first model to the simulated data and deriving a threshold-fit simulated index for the first model as a value of the index function for the first model that satisfies a threshold criterion; and a second maximizer module configured to derive an initial simulated index for the second model as an initial value of the index function for fitting the second model to the simulated data, wherein the analyzer module is further configured to derive an initial boundary for simulated index difference, wherein deriving the initial boundary for simulated index difference includes calculating a difference between the threshold-fit simulated index for the first model and the initial simulated index for the second model; determine, based on a comparison of the initial boundary for simulated index difference and the observed index difference, whether to update a counter used in calculating a simulated p-value; and select, based on the simulated p-value, one of the reference model and the alternative model for modeling the set of observed data.

In some embodiments, a non-transitory computer-readable medium stores a computer program, wherein the computer program, when executed by one or more computer processors, causes the one or more processors to execute a method for modeling a set of observed data.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings.

DETAILED DESCRIPTION

Figure 1:
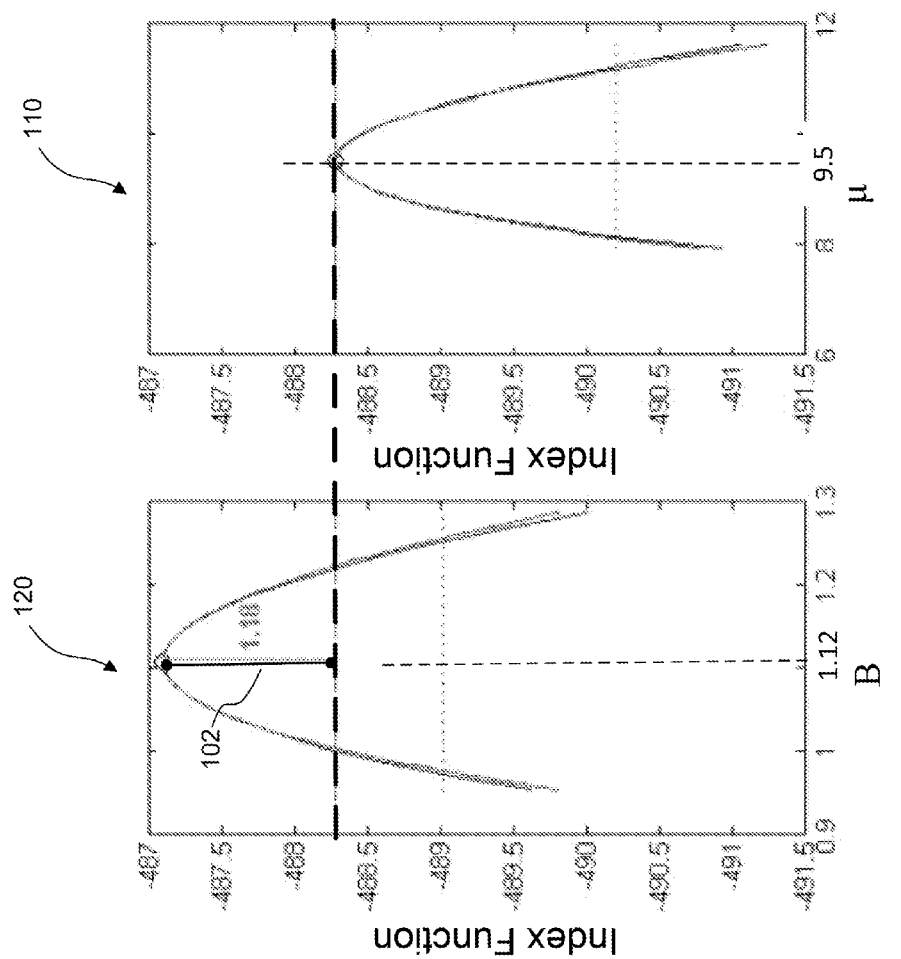
FIG. 1 shows a schematic for maximizing index functions according to some embodiments.

The following detailed description refers to the accompanying drawings. Wherever possible, the same reference numbers are used in the drawings and the description to refer to the same or similar parts. Also, similarly-named elements may perform similar functions and may be similarly designed, unless specified otherwise. Numerous details are set forth to provide an understanding of the described embodiments. The embodiments may be practiced without these details. In other instances, well-known methods, procedures, and components have not been described in detail to avoid obscuring the described embodiments. While several exemplary embodiments and features are described here, modifications, adaptations, and other implementations may be possible, without departing from the spirit and scope of the invention. Accordingly, unless stated otherwise, the descriptions relate to one or more embodiments and should not be construed to limit the invention as a whole. Instead, the proper scope of the invention is defined by the appended claims.

As used in this disclosure, a set can include one or more elements. Further, as used in this disclosure, a first variable is an increasing function of a second variable if the first variable does not decrease and instead generally increases when the second variable increases.

A comparison system compares at least two candidate models at a time. In some embodiments, a researcher needs to test a hypothesis by comparing a reference model with an alternative model. In some embodiments, the reference and the alternative models are two reduced versions of a full model with different sets of parameters. In some embodiments, one of the reference and the alternative models is the full model and the other one is a reduced model derived from the full model. In some embodiments, the reference and alternative models are not reduced versions of each other or of a full model and are instead different models used to describe the same data.

In some embodiments, a null hypothesis states that the reference model adequately describes the observed data. An alternative hypothesis, on the other hand, states that the reference model does not describe the data as well as the alternative model.

In some embodiments, when applying a model to a set of data, the comparison system determines values for the parameters for which the model best fits the data. To that end, the system utilizes an index function, which measures the fit of the model to the data for a specific choice of the parameters. In some embodiments, the index function is a log of the likelihood function. In some embodiments, the likelihood function is a density function, that is, the density of data under a corresponding model. In some embodiment, the index function includes one or more, or a linear combination of, an AIC (Akaike Information Criteria) function, a BIC (Bavesian Information Criteria) function, sum of square errors, an sum of absolute deviations.

In various embodiments, a likelihood function measures the probability or the probability density for a given set of data as a function of one or more unknown parameters. These parameters may be estimated by finding the values that maximize the likelihood.

In various embodiments, the observed data are presented in various formats, such as multidimensional matrices, text files, spread sheets, lists, or tables. In some embodiments the observed data are formulated as a response vector y. In the first example above, for instance, the response vector includes elements $y_{ijk}$ corresponding to the data for the cell indexed as i,j,k. In the second example above, the response vector includes elements $y_{ijk}$ corresponding to the reduction in blood pressure for patient i during visit j.

In some embodiments, the two models are represented as models M1 and M2, which respectively include parameter sets represented as vectors $\phi 1$ and $\phi 2$. Moreover, the index function for the two models are represented by $P(y|\phi 1, M1)$ and $P(y|\phi 2, M2)$. Thus, $P(y|\phi 1, M1)$ is the value of the index function for fitting model M1 to the response vector y with specific values selected for parameters $\phi 1$. Therefore, the null hypothesis, H0, states that the response y is a draw from the distribution $P(y|\phi 1, M1)$ for some unknown $\phi 1$. The alternate hypothesis H1, on the other hand, states that the response y is a draw from the distribution $P(y|\phi 2, M2)$ for some unknown $\phi 2$.

In some embodiments, the system computes the index value for different sets of values for the parameters and selects a set of values that provides the optimized index. In some embodiments, the optimized index is the largest index value. In some embodiments, an optimized index is the smallest index value. In such embodiments, a new index can be defined as the inverse or the negative of the existing index, such that that the optimized value for the new index is its largest value. For convenience, and without loss of generality, the optimized index will be called the maximized index.

Such set of values for the parameters in each model are called the fit parameters. Therefore, in the above formulation and in some embodiments, the fit parameters $\hat{\phi}_1$ and $\hat{\phi}_2$ satisfy maximization Equations (3a) and (3b)

$$\hat{\phi}_1 = \arg\max\nolimits_{\phi_1} \log P(y|\phi_1, M_1) \tag{3a}$$

$$\hat{\phi}_2 = \arg\max\nolimits_{\phi_2} \log P(y|\phi_2, M_2) \tag{3b}$$

Equation (3a) indicates that fit parameters $\hat{\phi}_1$ are the values of parameters $\phi_1$ that maximize index function P for fitting the first model $M_1$ to a set of data y. Similarly, Equation (3b) indicates that fit parameters $\hat{\phi}_2$ are the values of parameters $\phi_2$ that maximize index function P for fitting the second model M2 to the set of data y. When data y are the observed data $y_o$, the fit parameters are called observed fit parameters $\hat{\phi}_{1o}$ and $\hat{\phi}_{2o}$:

$$\hat{\phi}_{1o} = \arg\max\nolimits_{\phi_1} \log P(y_o|\phi_1, M_1) \tag{3c}$$

$$\hat{\phi}_{2o} = \arg\max\nolimits_{\phi_2} \log P(y_o|\phi_2, M_2) \tag{3d}$$

FIG. 1 shows a schematic for maximizing the index function and finding observed fit parameters according to some embodiments. In particular, FIG. 1 shows two graphs 110 and 120 of an index function as a function of parameters for two different models. Graph 110 shows values of the index function for fitting a reference model to the observed data for different values of a parameter μ of the reference model. Graph 120, on the other hand, shows values of the index function for fitting an alternative model to the observed data as a function of a parameter B of the alternative model.

Graph 110 shows that the set of observed fit parameter for the reference model is a value of μ=9.5. That is, for μ=9.5 the graph of the index function for fitting the reference model to the observed data reaches a maximum value of around −488.30. Graph 120, on the other hand, shows that the set of observed fit parameter for the alternative model is a value of B=1.12. That is, for B=1.12 the graph of the index function for fitting the alternative model to the observed data reaches a maximum value of around −487.12.

In some embodiments, the comparison system compares two models using the index function and the fit parameters. The system compares the two models by finding an observed index difference, that is, a difference in the index values for fitting each model to the observed data. To find the observed index difference, the system sets the parameters of each model to the observed fit parameters for the model.

In FIG. 1, for example, the alternative model reaches a higher index value compared to the reference model for fitting the observed data. More specifically, the observed index difference between the alternative and the reference models, that is, the difference between the two maxima in graphs 110 and 120, has a positive value of +1.18 (−487.12−(−488.30)=1.18). The observed index difference is depicted in FIG. 1 by vertical bar 102.

In some embodiments, the observed index difference is called an observed test statistic $T_O$. Observed statistic $T_O$ is used to test various hypotheses. In some embodiments the formulations of Equations 3(a)-(d), the observed index difference is calculated by Equation (4):

$$T_O = 2\{\log P(y_o|\hat{\phi}_{2o}, M_2) - \log P(y_o|\hat{\phi}_{1o}, M_1)\} \tag{4}$$

In Equation (4), to find the observed index difference $T_O$, the system subtracts the logarithm of the index function for the first model under the first set of observed fit parameters from the logarithm of the index function for the second model under the second set of observed fit parameters. $T_O$ is a quantification of how better the second model fits the observed data with respect to the first model. In various embodiments, instead of logarithms, the system uses another increasing function of the index function.

In some embodiments, if the alternative model has a smaller index value compared to the reference model, the alternative hypothesis will be rejected. If the alternative model has a larger index value, on the other hand, the null hypothesis is not necessarily rejected.

In general, a higher index value for a second model may indicate that the second model better describes the observed data. The higher index value for the second model, however, may not hold up under a different set of data. Instead, a higher index value for the second model may correspond to a statistical fluctuation of the index value for data that can be described as well or better by the first model.

Thus, in the above embodiments, a positive value for $T_O$ may or may not invalidate the null hypothesis. The system may determine the significance of the higher index value compared to statistically random fluctuations of the index function under the reference model. In some embodiments, the comparison system determines the significance of a positive $T_O$ by comparing it against a statistical distribution of the index difference under the null hypothesis. To that end, in some embodiments, the comparison system performs multiple simulations to generate random data based on the null hypothesis. For each set of randomly generated simulation data, the system finds the fit parameters and the maximum simulated index for each model under the fit parameters. For each simulation, the system then derives the difference in these index maxima, as a simulated index difference. The system then compares the derived simulated index differences with the observed index difference.

In the formulations of Equations (3) and (4), for example, in some embodiments the simulated index difference for one set of simulated data is calculated as $T_S$ from Equation (5):

$$T_S = 2\{\log P(y_{sim}|\hat{\phi}_{2s}, M_2) - \log P(y_{sim}|\hat{\phi}_{1s}, M_1)\} \tag{5}$$

In Equation (5), $y_{sim}$ is the set of simulation data generated in one simulation. In one embodiment, for example, $y_{sim}$ is drawn from the density $P(y|\hat{\phi}_1, M_1)$. Further, in equation (5), $\hat{\phi}_{1s}$ and $\hat{\phi}_{2s}$ are fit parameters found by maximizing the index function for the first and second models for fitting the simulation data, and thus $P(y_{sim}|\hat{\phi}_{2s}, M_2)$ and $P(y_{sim}|\hat{\phi}_{2s}, M_2)$ are simulated index maxima for the two models. The comparison model derives $T_S$ for each set of simulation data and compares the $T_S$ value with the $T_O$. In particular, the comparison system calculates a p-value for testing the null hypothesis compared to the alternative hypothesis by finding the probability that $T_S$ is larger than or equal to $T_O$, as shown in Equation (6):

$$P(T_O) = \text{Prob.}(T_S \geq T_O) \tag{6}$$

In some embodiments, the comparison system approximates the p-value for $T_O$ from the results of a number of simulations using Equation (7):

$$P(T_o) = \frac{1 + \sum_{i=1}^{n_{sim}} I(T_s^i \geq T_o)}{1 + n_{sim}} \tag{7}$$

In Equation (7), "i" is an index for the simulation running from 1 to the total number of simulations, $n_{sim}$, and $T_s^i$ is the value of $T_S$ derived from the $i^{th}$ simulation. I ($T_s^i \geq T_o$) is a step function that has a value of one whenever a simulated index difference $T_s^i$ for a simulation is equal to or greater than the observed index difference $T_o$, and otherwise has a value of zero. Equation (7), thus, essentially finds the proportion of simulations in which $T_s^i \geq T_o$ to the total number of simulations.

In some embodiments, the comparison system either rejects or fails to reject the null hypothesis based on the p-value. For example, in some embodiments, a significance level a is selected. The significance level indicates the allowed level of deviation from zero for the observed index difference under the null hypothesis. In various embodiments, a has values such as 0.10, 0.05, or 0.01. In some embodiments, the comparison system rejects the null hypothesis if the p-value is less than or equal to the significance level.

Figure 2A:
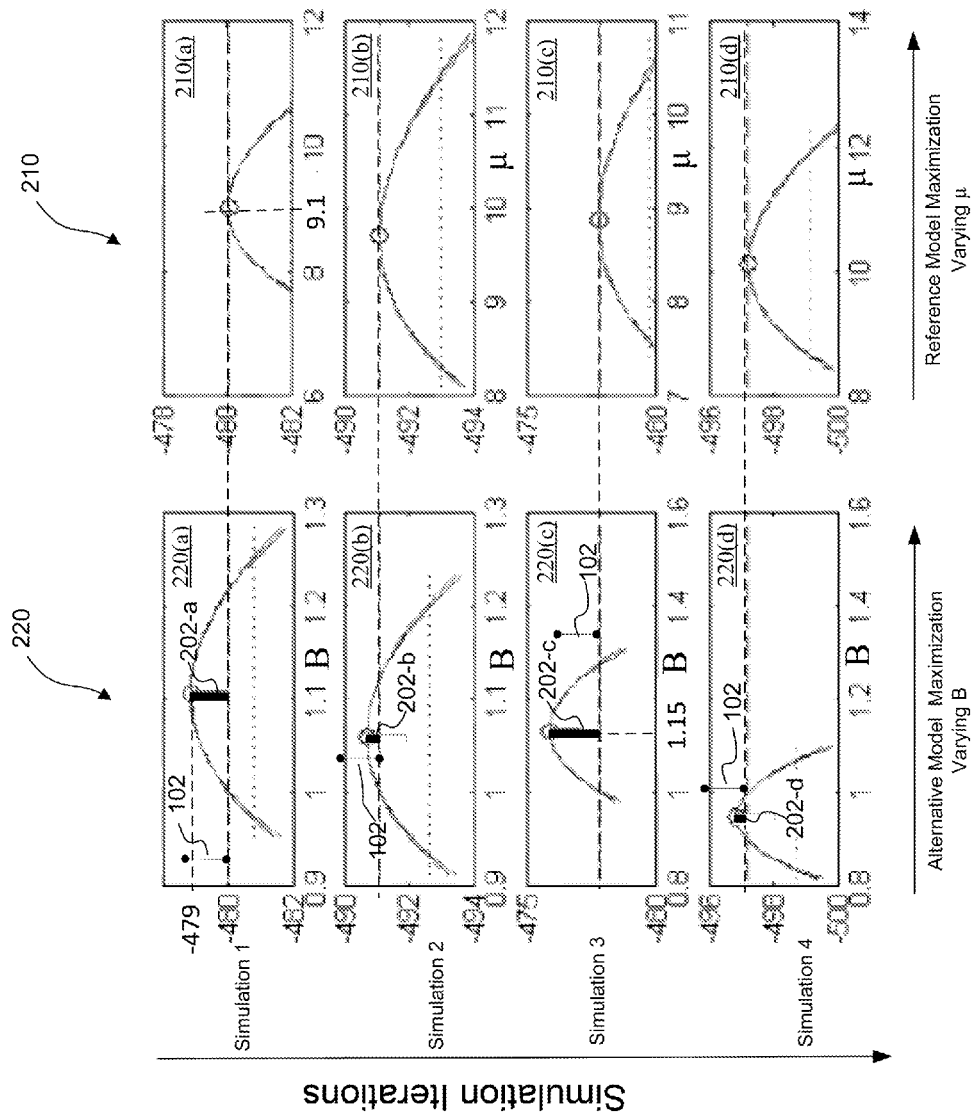
FIGS. 2A and 2B depict the processes of maximizing the index function in a simulation according to some embodiments.
Figure 2B:
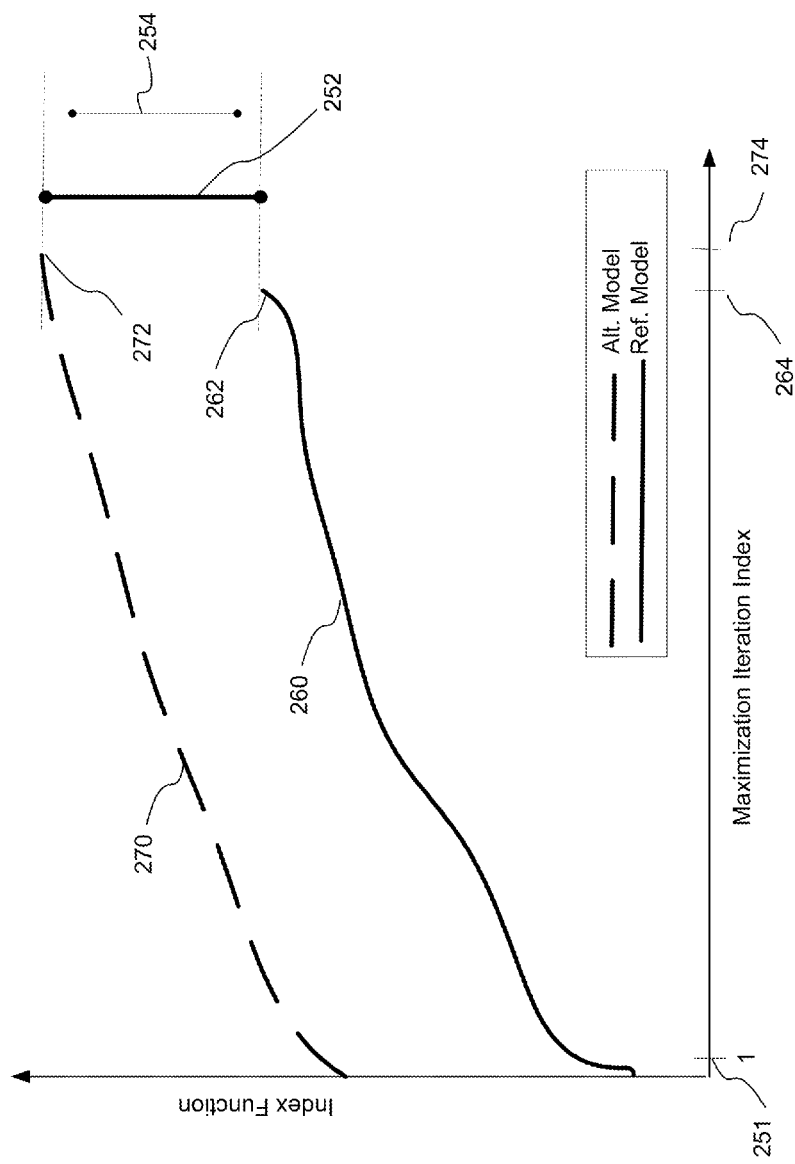

FIGS. 2A and 2B depict the processes of maximizing the index function in each simulation and deriving simulated index differences according to some embodiments. FIG. 2A shows a schematic for running four simulations and comparing the corresponding simulated index differences with the observed index difference for the models discussed in FIG. 1, according to some embodiments. FIG. 2B, on the other hand, shows schematic graphs for the process of maximizing the index function in each simulation for each model according to some embodiments.

FIG. 2A shows four graphs 210(a)-210(d) of the index function for fitting the reference model to four different sets of simulated data as functions of the reference parameter μ. Further, FIG. 2A shows four graphs 220(a)-220(d) of the index function for fitting the alternative model to the four sets of simulated data as functions of the alternative parameter B.

Graphs 210(a) and 220(a), for example, show the results of fitting the reference and alternative models to the first set of simulated data. Based on this fitting, the system determines simulated fit parameters and derives the corresponding simulated index difference. Graph 210(a) shows the values of the index function for fitting the reference model to the first set of simulated data for different values of the parameter μ of the reference model. Similarly, graph 220(a) shows the values of the index function for fitting the alternative model to the first set of simulated data for different values of the parameter B of the alternative model. Graph 210(a) shows that the index function for fitting the reference model to the first set of simulated data reaches a maximum value of −480.0 for the simulated fit parameter value of μ=9.1. Graph 220(a), on the other hand, shows that the index function for fitting the alternative model to the first set of simulated data reaches a maximum value of −479.0 for B=1.1. Thus, based on the first set of simulated data, the maximum simulated indexes for the reference and alternative models are respectively −480.0 and −479.0. The difference between these two simulated index maxima is the simulated index difference, shown by bar 202-a, and has a value of 1.0.

In some embodiments, the comparison system performs a set of iterations to find the maximum of the index function for each model. FIG. 2B shows two graphs depicting the processes of finding the index function maxima through such maximization iterations according to some embodiments. In FIG. 2B, the horizontal axis represents discrete values of successive maximization iterations, starting from 1 (for the first iteration) to a maximum iteration number for each model. The vertical axis represents values of the index function for each iteration.

In FIG. 2B, two illustrative index graphs 260 and 270 show the values of the index function for the reference and alternative models. The index graph for each model is derived by iterating over different values of the set of parameters for the model. For each set of parameters, the system derives the value of the index function for fitting the model to the set of data. In various embodiments, the set of data are a set of simulated data generated in a simulation. In some embodiments, in the first iteration 251, the set of parameters for each model is initialized as the set of observed fit parameters for that model. Further, in some embodiments such as those shown in FIG. 2B, the index function for each model is an increasing function of the iteration number. That is, the set of parameters for each iteration is selected such that the value of index function is equal to or larger than its value for the previous iteration. In some embodiments, the iteration for each model ends at a last iteration in which the index function reaches a maximum value. In some embodiments, the iteration for one or both models ends when the index function reaches a threshold value or when the number of iterations reaches a preset maximum iteration number.

In some embodiments, the iterations for each model are based on changing the value of the set of parameters for that model. In some embodiments, the iterations for the two models are performed independent of each other. In FIG. 2B, for example, index graph 260 for the reference model is derived independent of index graph 270 for the alternative model. Index graph 260 reaches its maximum point 262 at the last iteration 264 for the reference model, and index graph 270 reaches its maximum point 272 at the last iteration 274 of the alternative model. In some embodiments, last iterations 264 and 274 for the two models are derived independent of each other. In various embodiments, last iterations 264 and 274 may have the same or different values. In some embodiments, the iterations for the two models are performed using different processors and in parallel with each other.

In some embodiments, the comparison system uses the maxima of graphs 260 and 270 to derive the simulated index difference. In FIG. 2B these maxima are shown by points 262 and 272. The difference between these two values, shown as vertical bar 252, is the simulated index difference for the simulated data. Similarly, in graphs 210(a) and 220(a) of FIG. 2A, the maxima for the reference and alternative models are −480 and −479, respectively, and the simulated index difference is +1.0, shown by vertical bar 202-a.

Each simulated index difference can be compared with the observed index difference. Each graph in FIG. 2A includes, for comparison, a vertical bar 102 that has a value of 1.18 indicating the observed index difference derived in FIG. 1. Also, in FIG. 2B, an illustrative observed index difference is shown by vertical bar 254.

Accordingly, graph 210(a) shows that for the first simulation, simulated index difference 202-a is smaller than observed index difference 102. Similarly, FIG. 2B shows that for the illustrative simulated data of FIG. 2B, simulated index difference 252 is larger than observed index difference 254.

By repeating the simulations, the system finds a distribution of simulated index differences. In FIG. 2A, for example, processes similar to the above-described process of the first simulation is performed in the second, third, and fourth simulations to derive observed index differences shown by bars 202-b, 202-c, and 202-d. Comparing these values with the observed index difference 102 shows that, in the example of FIG. 2A, the simulated index difference is larger than the observed index difference for the third simulation; and that the simulated index difference is smaller than the observed index difference for first, second, and fourth simulations. In some embodiments, the comparison system inserts these results in Equation (7) to derive the p-value for the observed index difference.

In some embodiments, the above process is computationally intensive. For example, as shown in FIG. 2B, finding the fit parameters for each simulation and for each model requires maximizing the index function for that model through several maximization iterations. In some embodiments, the comparison system provides an efficient method for comparing two or more models. In some embodiments the comparison system reduces the computational requirements for finding the distribution of simulated index differences, comparing the observed index difference with the distribution of simulate index differences, or deriving the p-value. In some embodiments, a comparison system performs the comparison without performing the complete maximization of the index function for both models in each iteration.

Figure 3:
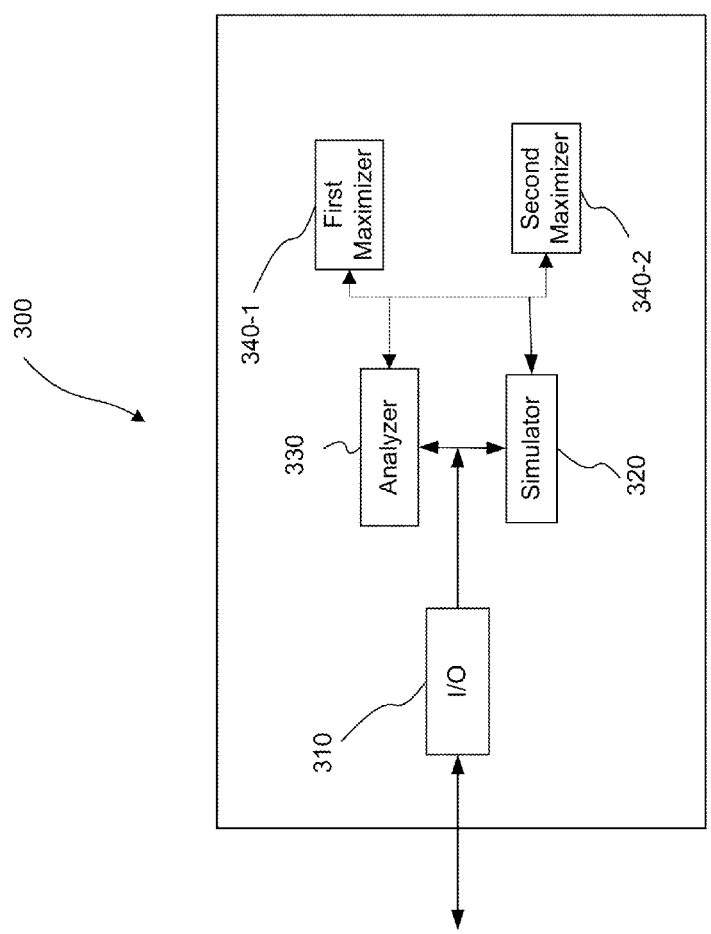
FIG. 3 shows a block diagram of a comparison system according to some embodiments.

FIG. 3 shows a block diagram of a comparison system 300 according to some embodiments. System 300 includes an input/output (I/O) module 310, a simulator module 320, an analyzer module 330, and first and second maximizer modules 340-1 and 340-2.

I/O module 310 receives information or commands from, and transmits outputs or results to, one or more external systems or users. In some embodiments, the received information includes information about various models, observed data, or the index function. In some embodiments, the outputs include results of comparing an observed index difference with a distribution of simulated index differences. In some embodiments, the outputs include a p-value for a null hypothesis against an alternative hypothesis derived based on observed and simulated data. In some embodiments, the outputs include a confidence interval on the true p-value.

Simulator module 320 derives simulated data. In some embodiments, simulator module 320 transmits the simulated data to first or second maximizers 340-1 or 340-2, or to analyzer module 330. In some embodiments, the simulations are based on the input data.

In various embodiments, first maximizer 340-1, second maximizer 340-2, or both perform the process of maximization of the index function for fitting a model to a set of observed data or a set of simulated data. In various embodiments, the first and second maximizers perform their respective maximizations in parallel or in series. In some embodiments, the maximizer receives the simulated data from simulator module 320 or receives the index function from analyzer module 330. In some embodiments, to perform a maximization, first maximizer 340-1 or second maximizer 340-2 calculates the value of the index function for fitting a model to the data for several different values of the set of parameters for the model, as depicted in FIG. 2A or FIG. 2B. The maximizer then finds the set of fit parameters for which the index function reaches a maximum. In some embodiments, instead of finding the maximum, the maximizer finds a set of fit parameters for which the index function exceeds a threshold value. In some embodiments, such operations are called threshold-fitting and the resulting index value a threshold-fit index value. In some embodiments, the maximizer transmits the results to analyzer module 330.

Analyzer module 330 analyzes the simulated data and maximization results and accordingly compares the two models. In some embodiments, analyzer module 330 compares two models by calculating a p-value for the observed index difference.

In some embodiments, the comparison system reduces the computational load for finding the p-value by as much as fifty percent. In some embodiments, in each simulation the comparison system eliminates the need for finding the maximum of the index function for at least one of the two models.

Figure 4A:
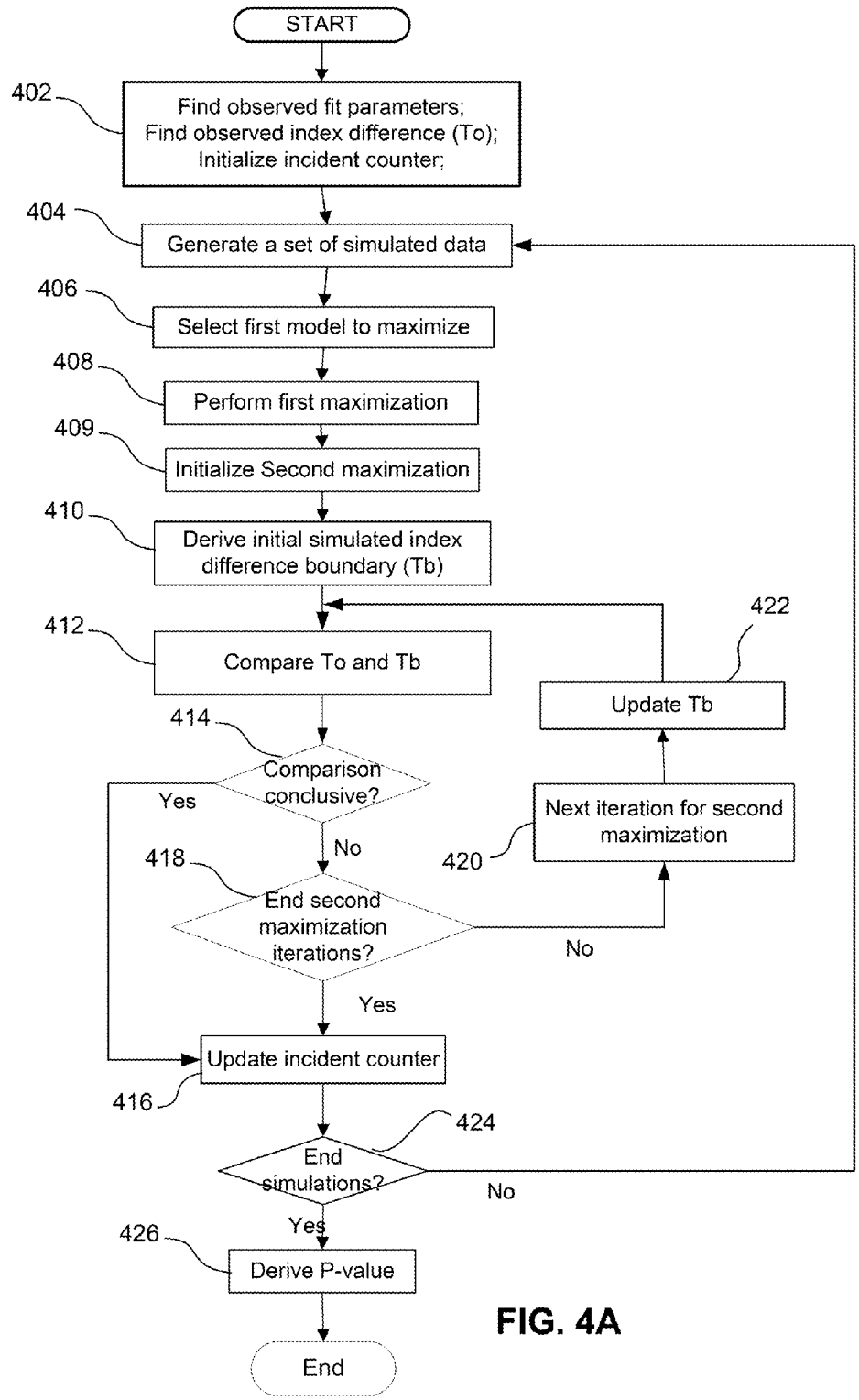
FIGS. 4A-4C show exemplary methods calculating the p-value according to some embodiments.
Figure 4B:
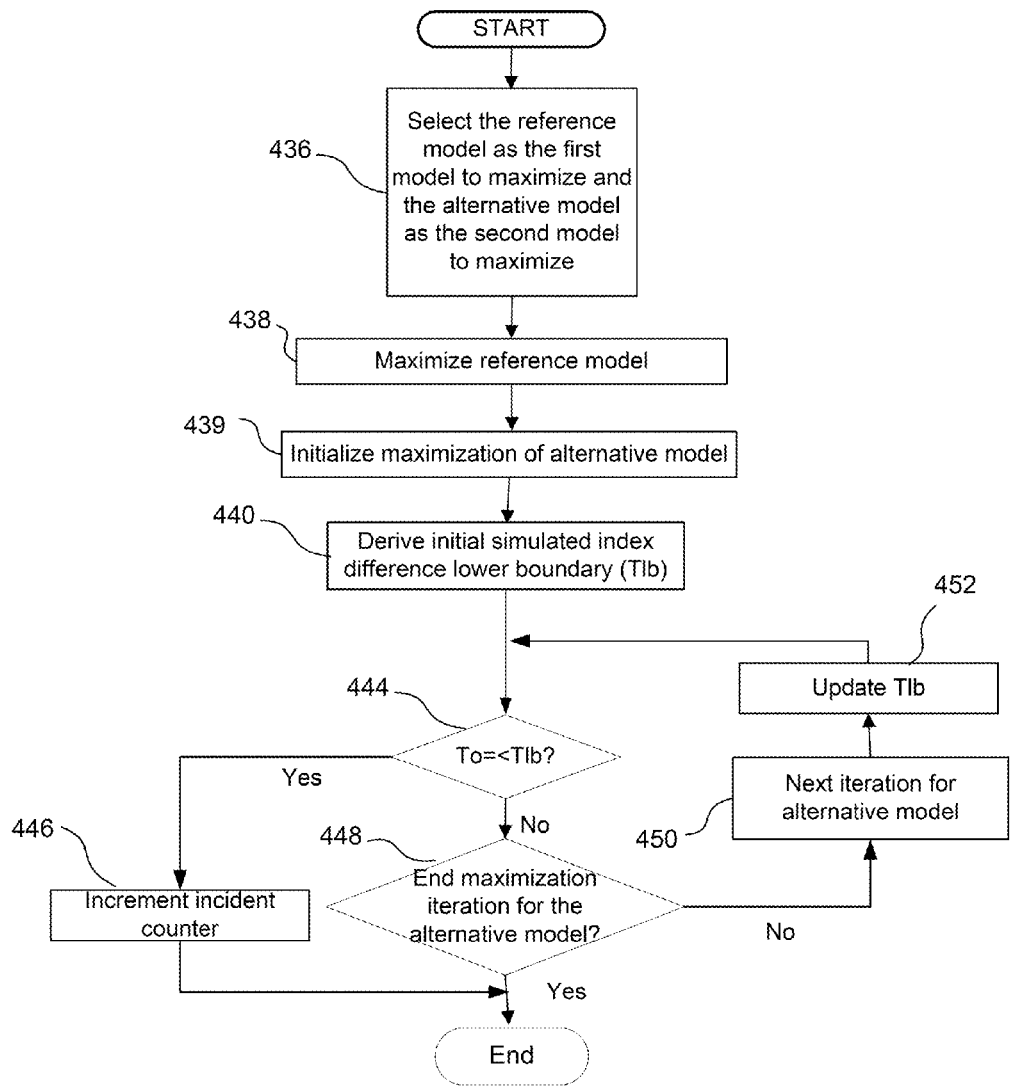
Figure 4C:
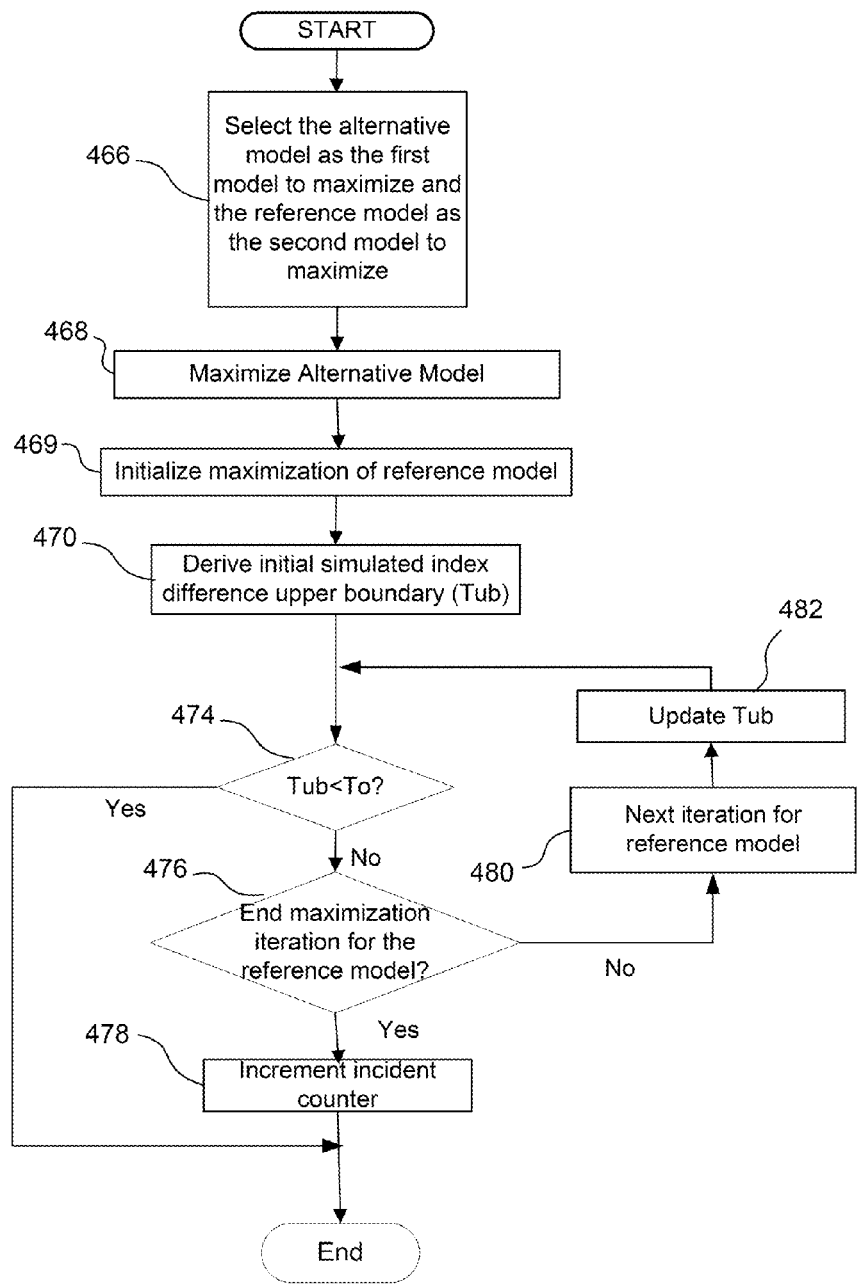

FIGS. 4A-4C illustrate exemplary processes for calculating the p-value according to various embodiments. In some embodiments, the methods shown in FIGS. 4A-4C are performed by a comparison system, such as system 300 in FIG. 3. FIG. 4A illustrates an exemplary process in which the system finds a lower bound or an upper bound for the simulated index difference. FIG. 4B shows in more detail a process in which the system finds a lower bound and FIG. 4C shows in more detail a process in which the system finds an upper bound.

In block 402, the system performs initialization before starting simulations, according to some embodiments. In particular, the system finds the observed fit parameters for the reference model and for the alternative model. In various embodiments, the system finds the observed fit parameters by maximizing the index function for fitting the corresponding model to the observed data. The system uses the observed fit parameters to calculate the observed index difference ($T_O$). The system initializes an incident counter. In some embodiments, the incident counter counts the number of times that a simulated index difference is equal to or greater than the observed index difference. In some embodiments, in each simulation the incident counter is the cumulative values of $I(T_s^i \geq T_o)$ in Equation (7) for all simulation up to the present. That is, in a simulation j, the incident counter is the value of $\Sigma_{i=1}^{j} I(T_s^i \geq T_o)$ as used in Equation (7). In some embodiments, the system initializes the incident counter by setting it to zero before starting the simulations.

After initialization in block 402, the system performs one or more simulation iterations. A generalized simulation loop, including one or more simulation iterations, is described by the process starting at block 404 and ending at block 424. A simulation iteration in the loop includes steps described in block 406, 408, 409, 410, 412, 414, 416, 418, 420, and 422. More specific embodiments of the simulation loop are described in FIGS. 4B and 4C. For each simulation iteration, the system generates a new set of simulated data. Based on the simulated data, the system determines whether the simulated index difference is equal to or greater than the observed index difference, and accordingly updates the incident counter.

In block 404, the system generates a new set of simulated data for a s simulation iteration. In some embodiments, simulator module 320 generates the new set of simulated data under the null hypothesis with known parameters. In some embodiments, the simulator module generates the new set of simulated data as a random set of data based on the fitted reference model.

In block 406, the system selects one of the reference and alternative models as the first model to maximize. For ease of reference, in FIG. 4A the model selected in block 406 is referred to as the first model and the other model is referred to as the second model. In some embodiments, the analyzer module selects the first model from among the reference and the alternative models based on results of previous simulations, if any. In some embodiments, the analyzer module randomly selects the first model from among the reference and the alternative models. In some embodiments, the analyzer module generates a random number and compares that random number with a number derived from previous simulations. Based on the result of the comparison, the analyzer module selects the first model from among the reference and the alternative models.

In block 408, the system performs a first maximization. In some embodiments, the first maximizer module performs the first maximization. In some embodiments, the first maximization includes finding a maximum of the index function for fitting the first model to the simulated data. In some embodiments, the first maximization includes varying the set of parameters for the first model and finding a set of fit parameters for the first model. In some embodiments, the first maximization includes calculating the maximum simulated index for the first model in the manner described in FIG. 2A or in FIG. 2B. Based on the results of the first maximization, the maximizer module derives a maximum simulated index for the first model.

In some embodiments, the first maximizer module performs the first maximization by finding values of the parameters for which the index function reaches a threshold value or the number of iterations reaches a maximum iteration number. In some embodiments, the threshold value is a value of the index function that is equal to or close to a known maximum of the index function. In some embodiments, the first maximizer module ends the maximization iterations when the value of the index function reaches or exceeds the threshold value. In some embodiments, such an operation is called threshold-fitting and the resulting index value is called a threshold-fit index value. The maximizer module may use the threshold-fit index value as the maximum simulated index for the first model.

In block 409, the system initializes the second maximization. In some embodiments, block 409 is performed by the analyzer module. In some embodiments, to initialize the second maximization, the system calculates an initial simulated index for the second model. In some embodiments, the initial simulated index for the second model is the value of the index for the first iteration of the maximization iteration, as shown in FIG. 2B. That is, the system finds the initial simulated index for the second model by setting the parameters for the second model to its observed fit parameters and finding the index function for fitting the second model to the simulated data.

In block 410, the system derives an initial boundary value for the simulated index difference ($T_b$). The system derives the initial boundary value for the simulated index difference by finding a difference between the maximum simulated index for the first model and the initial simulated index for the second model.

In some embodiments, such as those detailed in FIG. 4B, the initial boundary value is a lower boundary value for the simulated index difference. Such a lower boundary value indicates that maximizing the second model will result in a value of the simulated index function that cannot be smaller than the lower boundary. Alternatively, in some embodiments such as those detailed in FIG. 4C, the initial boundary value is an upper boundary value for the simulated index difference. Such an upper boundary value indicates that maximizing the second model will result in a value of the simulated index function that cannot be larger than the upper boundary.

The system performs a second maximization iteration loop for the second model, which includes blocks starting at 412 and ending at 422, according to some embodiments. As explained above, in some embodiments the first iteration of the second maximization is performed in block 409 by initializing the set of parameters for the second model to the observed fit parameters. Further, as explained below in more detail, if necessary the system performs further iterations of the second maximization. The system may terminate the iterations, upon performing the first iteration or a subsequent iteration, if a conclusive decision can be made based on the results of the latest iteration. Otherwise, the system terminates the iterations upon reaching the last iteration.

In block 412, the system compares the observed index difference ($T_O$) with the initial boundary value for the simulated index difference ($T_b$). In some embodiments, block 412 is performed by the analyzer module. In some embodiments, block 412 includes determining whether $T_O$ is greater than, equal to, or smaller than $T_b$.

In decision block 414, the system determines whether the comparison results in a conclusive decision based on the simulated data. In some embodiments, decision block 414 is performed by the analyzer module. In some embodiments, the system determines whether any further iterations of the second maximization is needed. In some embodiments, a conclusive decision includes determining that the relationship between the observed index difference and simulated index difference can be found without performing any further iterations of the second maximization. For example, in some embodiments such as those related to FIG. 4B in which $T_b$ is a lower boundary, a conclusive decision can be made if $T_O$ is smaller than $T_b$. Alternatively, in some embodiments such as those related to FIG. 4C in which $T_b$ is an upper boundary, a conclusive decision can be made if $T_O$ is larger than $T_b$.

If a conclusive decision can be made at this stage (decision block 414: Yes), in block 416 the system updates the incident counter based on that decision. As detailed below in relation to FIGS. 2B and 2C, in different cases the system either increments the incident counter or leaves its value unchanged.

If a conclusive decision cannot be made at this stage (decision block 414: No), in decision block 418 the system determines whether to end the second maximization iteration. In some embodiments, the second maximization iteration ends upon reaching its last iteration, such as last iterations 264 or 274 in FIG. 2B. In various embodiments, the last iteration is reached if the maximum of the index function for the second model is found, the last allowable iteration has been performed, or the index value reaches a threshold value.

If the second maximization has not reached its last iteration (decision block 418: No), the system performs the next iteration of the second maximization in block 420. In some embodiments, the next iteration includes updating the values of the set of parameters for the second model and deriving a new value of index function for fitting the second model to the simulated data. The new value is stored as an updated simulated index for the second model. In some embodiments, such as those shown in FIG. 2B, the updated values of the set of parameters are chosen such that each consecutive iteration increases the value of the index function.

In block 422, the system updates the boundary value for the simulated index difference ($T_b$). In some embodiments, block 422 is performed by the analyzer module. In some embodiments, the system updates $T_b$ by finding a difference between the maximum simulated index for the first model and the updated simulated index for the second model, as derived in block 420. The system then loops back to block 412, by comparing the updated $T_b$ with the observed index difference $T_O$.

If the second maximization reaches its last iteration (decision block 418: Yes), the system moves to block 416 and updates the incident counter based on the completion of the second maximization iteration. As detailed below in relation to FIGS. 2B and 2C, in different cases and based on this completion, the system either increments the incident counter or leaves its value unchanged.

In some embodiments, the system performs the first maximization (block 408) and the second maximization (starting at block 409 and ending at block 422) in parallel. In some embodiments, the system drives $T_b$ once one of the two maximizations are ended and based on the latest value of the index function in the second maximization. The system then decides whether to end the second maximization or continue it based on whether the system can make a conclusive decision based on the value of $T_b$.

In some embodiments, the system compares more than two models by using parallel computing. In doing so, each parallel thread performs the maximization of the index function for one of the models and the analyzer module compares the results of various maximizations at different stages of one or more maximizations in the manner described herein.

Upon exiting the maximization iteration for each simulation, in decision block 424 the system decides whether the simulation loop should be ended. In some embodiments, the system ends the simulation loop if a pre-set number of simulations is performed. In some embodiments, the system ends the simulation loop if the results of previous simulations indicate that a decision can be made about the hypotheses. In some embodiments, the system ends the simulation loop if the results of previous simulations indicates that the p-value has already exceeded the significance level a, or that the p-value can never reach the significance level a even if the remaining simulations all increase the incident counter. In some embodiments, for example, the simulations are stopped if a ratio of the incident counter to the number of already performed simulations reaches a threshold value. In some embodiments, the simulations are stopped if a ratio of the incident counter to the total number of simulations is below a lower threshold or exceeds an upper threshold.

If the system does not end the simulation loop (decision block 424: No), the system loops back to block 404 and starts a new simulation by generating a new set of simulated data. On the other hand, if the system ends the simulation loop (decision block 424: Yes), in block 426 the system derives the p-value. In some embodiments, the system derives the p-value based on the value of the incident counter. In some embodiments, the system derives the p-value by using Equation (7).

FIG. 4B shows a process for an embodiment in which a lower boundary for the simulated index difference is found. For such an embodiment, FIG. 4B shows details of one simulation iteration as more generally discussed in FIG. 4A. Further, FIGS. 5A and 5B show illustrative index graphs derived in each such simulation iteration.

In block 436, the system selects the reference model as the first model and the alternative model as the second model to maximize. In other embodiments, as detailed below, the system makes such a selection by comparing a randomly generated number with a pre-set number or with a number derived from the results of previous iterations.

In block 438, the system performs the first maximization by deriving the maximum simulated index for the reference model. In various embodiments, such a first maximization is performed in the manner described in relation to graphs 210(a)-210(d) of FIG. 2A, graph 260 of FIG. 2B, or graph 510 of FIG. 5A.

Figure 5A:
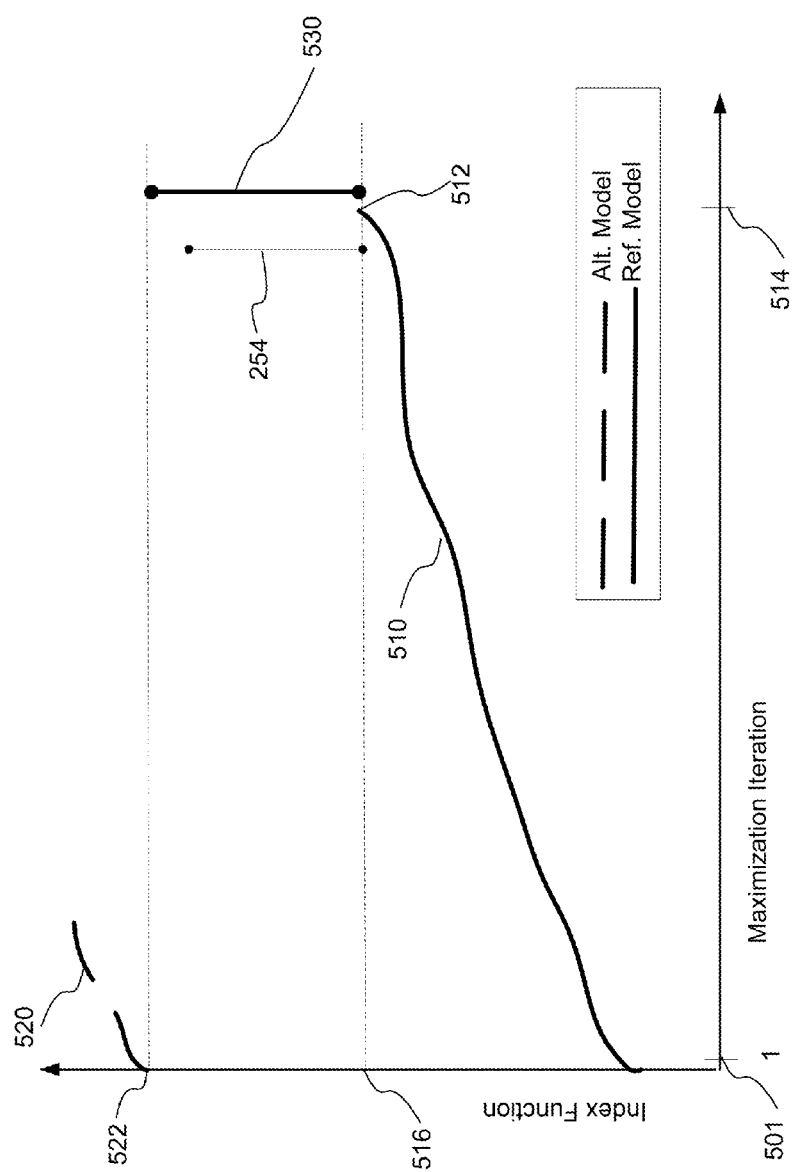
FIGS. 5A and 5B show index graphs for deriving a lower boundary for the simulated index difference according to some embodiments.
Figure 5B:
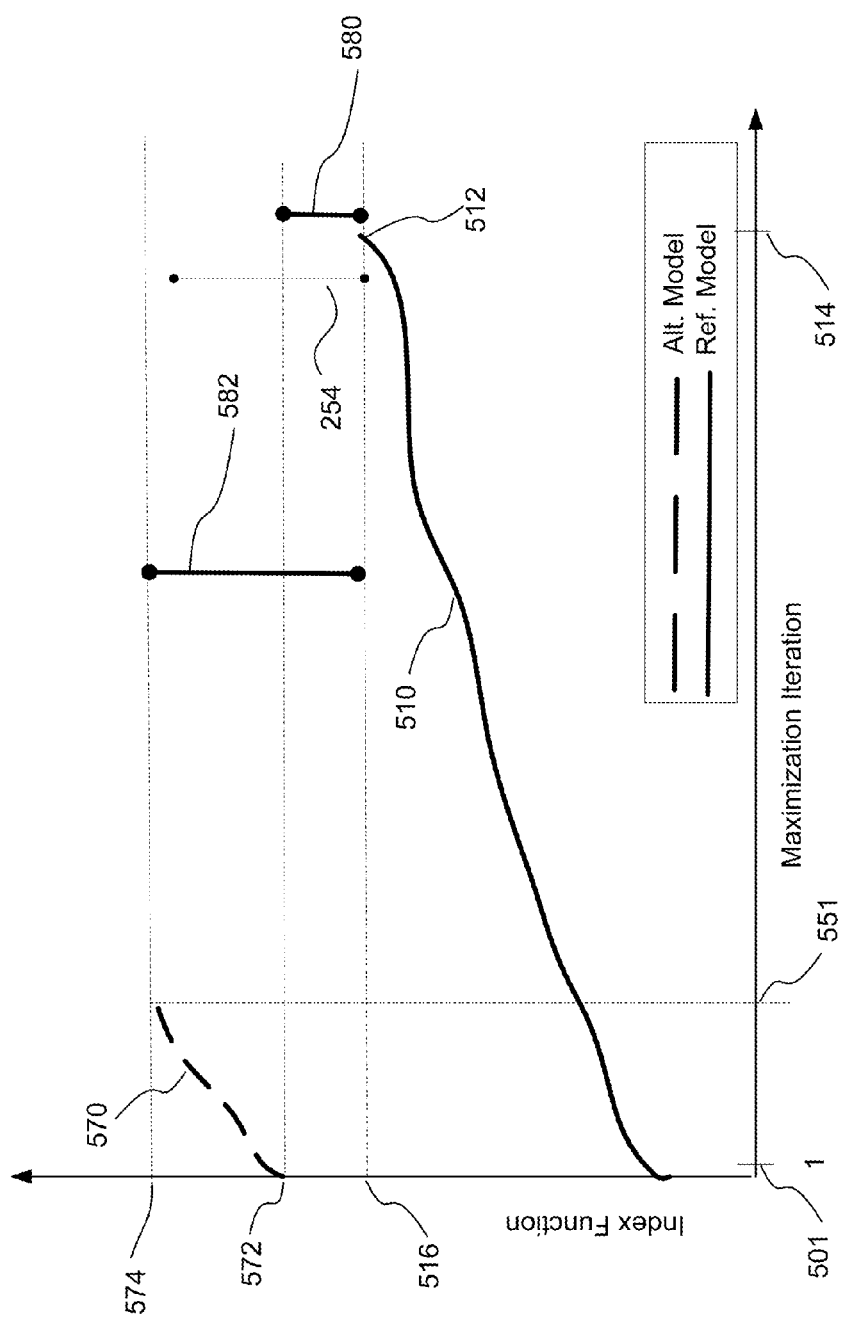

Referring to FIG. 5A, it includes graph 510, which is an index graph for the reference model. Index graph 510 reaches its maximum point 512 at the last iteration 514 for the reference model. The maximum value 516 of the index function for the reference model at maximum point 512 is the maximum simulated index for the reference model.

Returning to FIG. 4B, in block 439 the system initializes maximization of the alternative model. In some embodiments, to initialize this maximization, the system derives an initial simulated index for the alternative model. In some embodiments, the system derives the initial simulated index for the alternative model by setting the parameters for the alternative model to its observed fit parameters and finding the index function for fitting the alternative model to the simulated data.

In FIG. 5A, graph 520 (at the upper left corner of FIG. 5A) is an index graph for the alternative model. For illustration, FIG. 5A shows a section of graph 520. As explained below, however, in the embodiment shown in FIG. 5A the system need not find the values of this graph beyond a first iteration 501. At first iteration 501, index graph 520 starts at an initial value 522. Initial value 522 is derived by finding the index function for fitting the alternative model to the simulated data using the observed fit parameters for the alternative model. The initial value 522 of the index function for the alternative model is the initial simulated index for the alternative model.

Returning to FIG. 4B, in block 440 the system derives an initial lower boundary for the simulated index difference ($T_S^{LB}$). In some embodiments, the system derives the initial $T_S^{LB}$ by subtracting the maximum simulated index for the reference model from the initial simulated index for the alternative model. In FIG. 5A, the difference between the initial value 522 for the alternative model and the maximum value 516 for the reference model is the initial lower boundary for the simulated index difference, shown as vertical bar 530.

For each simulation iteration, the initial lower boundary for the simulated index difference of this simulation iteration ($T_S^{LB}$) has a value that is generally lower than or at most equal to the simulated index difference (i.e., $T_S^i$ in Equation (7)). As seen in FIG. 5A, further maximization iterations for the alternative model increases the value of the index graph 520 for the alternative model and thus increases the difference between that value and the maximum simulated index 516 for the reference model.

Returning to FIG. 4B, in decision block 444 the system compares the initial $T_S^{LB}$ with the previously determined observed index difference ($T_O$). If $T_S^{LB}$ is larger than or equal to $T_O$, the system can conclusively decide that $T_S^i$ is also larger than or equal to $T_O$, because $T_S^i$ is larger than or equal to $T_S^{LB}$. In this case (decision block 444: Yes), the system increments the incident counter in block 446, and exits the maximization iterations for the alternative model.

Such an early stop of the second maximization is shown in FIG. 5A. In FIG. 5A, vertical bar 254 indicates, for reference, the value of the observed index difference $T_O$. In the exemplary case shown in FIG. 5A, the value of 254 is smaller than the value of 530, the initial lower boundary for simulated index difference ($T_S^{(i)LB}$). Thus, in the case of FIG. 5A, the system can stop the maximization iterations of the alternative model after its first maximization iteration.

If, on the other hand, $T_S^{(i)LB}$ is not larger than or equal to $T_O$ (decision block 444: No), the system cannot conclusively decide the relationship between the values of $T_S^i$ and $T_O$. The system thus proceeds to perform further maximization iterations for the alternative model.

In decision block 448 the system determines whether to end the maximization iteration for the alternative model. In some embodiments, this iteration ends upon reaching its last iteration, such as the last iteration 274 in FIG. 2B. In various embodiments, the last iteration is reached if the maximum of the index function for the alternative model is found or if the last allowable iteration for the alternative model has been performed. In some embodiments such as the one discussed in FIG. 5B, the maximization iteration for the alternative model ends if the system can make a conclusive decision based on an updated value of $T_S^{LB}$.

If the system decides not to end the maximization iteration for the alternative model (decision block 448: No), in block 450 the system performs the next iteration of the maximization for the alternative model. In some embodiments, the next iteration includes updating the values of the set of parameters for the alternative model and deriving a new value of the index function for fitting the alternative model to the simulated data. The system stores the new value as an updated simulated index for the alternative model. In some embodiments, such as the one shown in FIG. 5B, the updated values of the set of parameters are chosen such that each consecutive iteration increases the value of the index function.

FIG. 5B shows a case in which the initial lower boundary for the simulated index difference does not result in a conclusive decision, according to some embodiments. In FIG. 5B, graph 510 is a maximized index graph for the reference model. Moreover, graph 570 is an index graph for the alternative model. In FIG. 5B, the initial lower boundary is shown by vertical bar 580. This initial lower boundary is the difference between the value 572 (the initial simulated index for the alternative model) and the value 512 (the maximum simulated index for the reference model). In the case shown in FIG. 5B, this initial lower boundary 580 is smaller than the observed index difference 254. Therefore, in the embodiment shown in FIG. 5B, the system cannot make a conclusive decision based on the initial lower boundary (i.e., value of 580) derived from the first maximization iteration for the alternative model and proceeds to further maximization iterations for the alternative model.

Further maximization iterations for the alternative model result in values that are shown in graph 570. In some embodiments, each new iteration results in an updated value of the index function for the alternative model, which is larger than the index value in the previous iteration. As a result, as shown in graph 570 of FIG. 5B, the index function is an increasing function of the iteration.

Returning to FIG. 4B at block 452, after each such maximization iteration for the alternative model, the system updates the value of the lower boundary for the simulated index difference ($T_S^{LB}$). In some embodiments, the system updates $T_S^{LB}$ by subtracting the maximum simulated index for the reference model (value 516 in FIG. 5B) from the update simulated index for the alternative model (values on graph 570). The system then loops back to decision block 444 and compares the updated $T_S^{LB}$ with the observed index difference $T_O$.

In some embodiments, such as that shown in FIG. 5B, upon one or more maximization iterations for the alternative model, the system finds that the updated $T_S^{LB}$ s greater than or equal to $T_O$. In FIG. 5B, such a situation is reached at the iteration marked 551. At iteration 551, the index for the alternative model (graph 570) reaches a value 574. The difference between value 574 (the updated index value for the alternative model) and value 516 (the maximum index value for the reference model) results in an updated $T_S^{LB}$ shown as vertical bar 582. In this case, updated $T_S^{LB}$ (vertical bar 582) is larger than observed index difference 254.

Upon determining that the updated $T_S^{LB}$ is larger than or equal to $T_O$ (decision block 444: Yes), in some embodiments the system ends the maximization iterations for the alternative model. Such a situation is shown in FIG. 5B, in which the system ends updating graph 570 beyond iteration 551. Further, the system increments the incident counter in block 446.

The embodiments shown in FIGS. 5A and 5B are examples of early stop simulations. In these embodiments, for one set of simulated data, the system stops the maximization iterations for the alternative model before finding its maximum. Instead, the system makes a conclusive decision that the incident counter should be incremented based on results of an earlier iteration, i.e., at the first iteration (FIG. 5A) or at some subsequent iteration before the last maximization iteration for the alternative model (FIG. 5B).

In some embodiments, $T_S^{LB}$ remains below $T_O$ even when the system reaches the last maximization iteration for the alternative model (decision block 448: Yes). In such a situation, the system exits the maximization iteration without incrementing the incident counter. In some embodiments, such a situation occurs when the index function for the alternative model, such as graph 570 in FIG. 5B, reaches its maximum. In this case, the last updated index value for the alternative model is the maximum simulated index for the alternative model, and the last updated $T_S^{LB}$ is the simulated index difference $T_s^i$. In such a situation, the system can conclusively decide that the simulated index difference is smaller than the observed index difference $T_O$. Based on this conclusion, the system does not increment the incident counter for the present simulation data.

FIG. 4C shows a process for an embodiment in which an upper boundary for the simulated index difference is found. For such an embodiment, FIG. 4C shows details of one simulation iteration as more generally discussed in FIG. 4A. Further, FIGS. 6A and 6B show exemplary index graphs derived in each such simulation iteration.

In block 466, the system selects the alternative model as the first model and the reference model as the second model. In other embodiments, as detailed below, the system makes such a selection by comparing a randomly generated number with a pre-set number or with a number derived from the results of previous iterations.

In block 468, the system performs the first maximization by deriving the maximum simulated index for the alternative model. In various embodiments, such a first maximization is performed in the manner described in relation to graphs 220(a)-220(d) of FIG. 2A, graph 270 of FIG. 2B, or graph 620 of FIG. 6A.

Figure 6A:
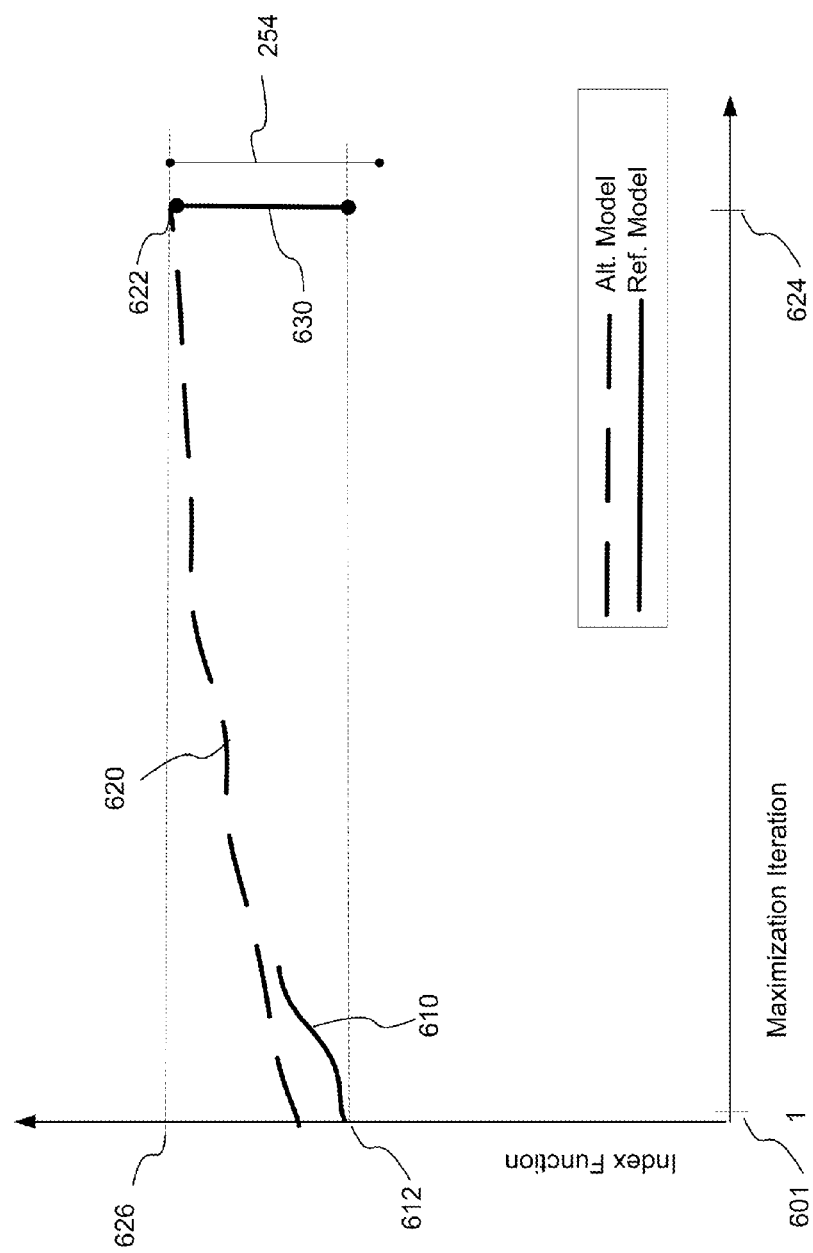
FIGS. 6A and 6B show index graphs for deriving an upper boundary for the simulated index difference according to some embodiments.
Figure 6B:
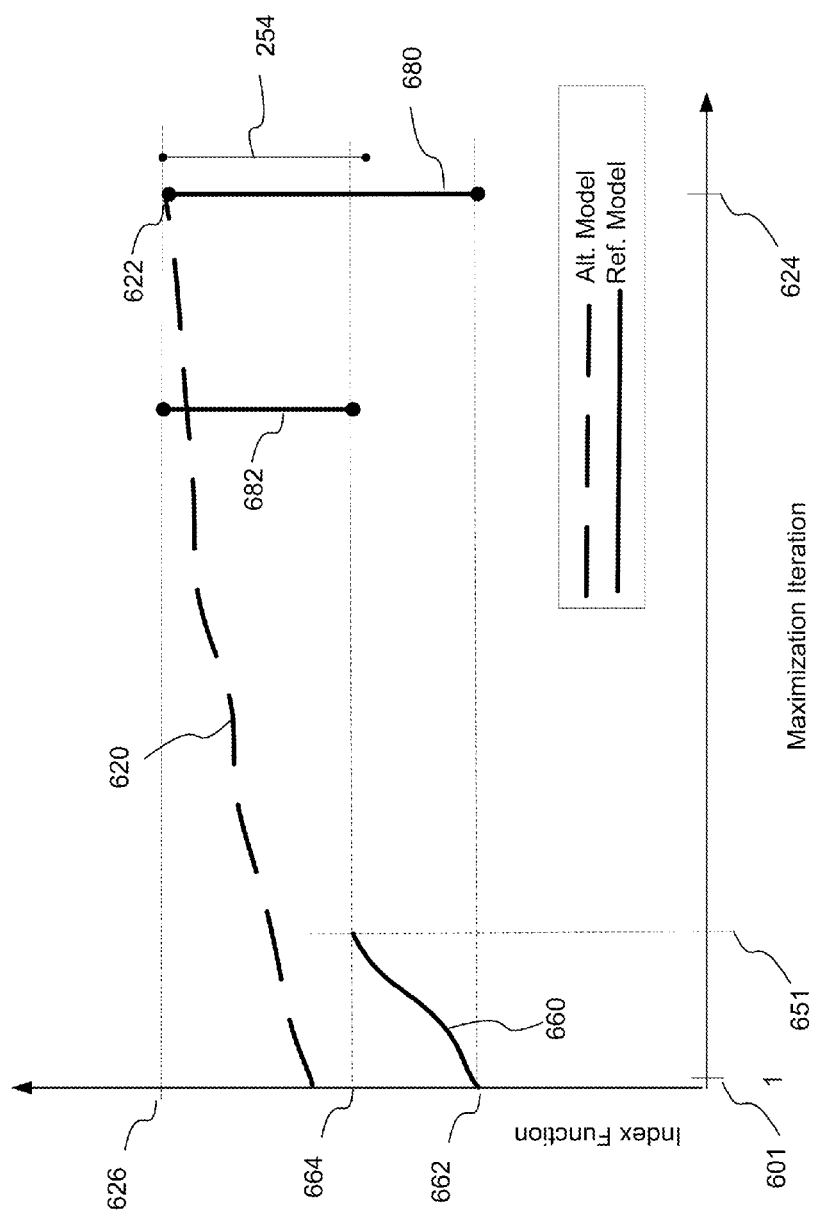

FIG. 6A includes graph 620, which is an index graph for the alternative model. Index graph 620 reaches its maximum point 622 at the last iteration 624 for the alternative model. The maximum value 626 of the index function for the alternative model at maximum point 622 is the maximum simulated index for the alternative model.

Returning to FIG. 4C, in block 469 the system initializes maximization of the reference model. In some embodiments, to initialize this maximization, the system derives an initial simulated index for the reference model. In some embodiments, the system derives the initial simulated index for the reference model by setting the parameters for the reference model to its observed fit parameters and finding the index function for fitting the reference model to the simulated data.

In FIG. 6A, graph 610 is an index graph for the reference model. For illustration, FIG. 6A shows a section of graph 610. As explained below, however, in the embodiment shown in FIG. 6A the system need not find the values of this graph beyond a first iteration 601. At first iteration 601, index graph 610 starts at an initial value 612. Initial value 612 is derived by finding the index function for fitting the reference model to the simulated data using the observed fit parameters for the reference model. The initial value 612 of the index function for the reference model is the initial simulated index for the reference model.

Returning to FIG. 4C, in block 470 the system derives an initial upper boundary for the simulated index difference ($T_S^{UB}$). In some embodiments, the system derives the initial $T_S^{UB}$ by subtracting the initial simulated index for the reference model from the maximum simulated index for the alternative model. In FIG. 6A, the difference between this maximum value 626 for the alternative model and the initial value 612 for the reference model is the initial upper boundary for the simulated index difference, shown as vertical bar 630.

The initial upper boundary for the simulated index difference ($T_S^{UB}$) has a value that is generally higher than or at least equal to the simulated index difference for this simulation iteration (i.e., $T_s^i$ in Equation (7)). As seen in FIG. 6A, further maximization iterations for the reference model increases the value of the index graph 610 for the reference model and thus decreases the difference between that value and the maximum simulated index 626 for the alternative model.

Returning to FIG. 4C, in decision block 474 the system compares the initial $T_S^{UB}$ with the previously determined observed index difference ($T_O$). If $T_S^{UB}$ is smaller than $T_O$, the system can conclusively decide that $T_s^i$ is also smaller than $T_O$, because $T_s^i$ is smaller than or equal to $T_S^{UB}$. In this case (decision block 474: Yes), the system can conclusively decide that $T_s^i$ is smaller than $T_O$ and stop the maximization iterations for the reference model without incrementing the incident counter.

Such an early stop of the second maximization is shown in FIG. 6A. In FIG. 6A, vertical bar 254 indicates, for reference, the value of the observed index difference $T_O$. In the exemplary case of FIG. 6A, the value of 254 is larger than the value of 630, the initial upper boundary for simulated index difference ($T_S^{UB}$). Thus, in the case of FIG. 6A, the system can stop the maximization iterations of the reference model after its first maximization iteration.

If, on the other hand, $T_S^{UB}$ is not smaller than $T_O$ (decision block 474: No), the system cannot conclusively decide the relationship between the values of $T_s^i$ and $T_O$. The system thus proceeds to perform further maximization iterations for the reference model.

In decision block 476 the system determines whether to end the maximization iteration for the reference model. In some embodiments, this iteration ends upon reaching its last iteration, such as the last iteration 264 in FIG. 2B. In various embodiments, the last iteration is reached if the maximum of the index function for the reference model is found or if the last allowable iteration for the reference model has been performed. In some embodiments, such as the one discussed in FIG. 6B, the maximization iteration for the reference model ends if the system can make a conclusive decision based on an updated value of $T_S^{UB}$.

If the system decides not to end the maximization iteration for the reference model (decision block 476: No), in block 480 the system performs the next iteration of the maximization for the reference model. In some embodiments, the next iteration includes updating the values of the set of parameters for the reference model and deriving a new value of the index function for fitting the reference model to the simulated data. The system stores the new value as an updated simulated index for the reference model. In some embodiments, such as the one shown in FIG. 6B, the updated values of the set of parameters are chosen such that each consecutive iteration increases the value of the index function.

FIG. 6B shows a case in which the initial upper boundary for the simulated index difference does not result in a conclusive decision, according to some embodiments. In FIG. 6B, graph 620 is a maximized index graph for the alternative model. Moreover, graph 660 is an index graph for the reference model. In FIG. 6B, the initial upper boundary is shown by vertical bar 680. This initial upper boundary is the difference between a value 662 (the initial simulated index for the reference model) and a value 626 (the maximum simulated index for the alternative model). In the case shown in FIG. 6B, this initial upper boundary 680 is larger than the observed index difference 254. Therefore, in the embodiment shown in FIG. 6B, the system cannot make a conclusive decision based on the initial upper boundary (i.e., value of 680) derived from the first iteration and proceeds to further maximization iterations for the reference model.

Further maximization iterations of the reference model result in values that are shown in graph 660. In some embodiments, each new iteration results in an updated value of the index function for the reference model, which is larger than the index value in the previous iteration. As a result, as shown in graph 660 of FIG. 6B, the index function is an increasing function of the iteration.

Returning to FIG. 4C at block 482, after each such maximization iteration for the reference model, the system updates the value of the upper boundary for the simulated index difference ($T_S^{UB}$). In some embodiments, the system updates $T_S^{UB}$ by subtracting the updated simulated index for the reference model (values on graph 660 in FIG. 6B) from the maximum simulated index for the alternative model (value 626). The system then loops back to decision block 474 and compares the updated $T_S^{UB}$ with the observed index difference $T_O$.

In some embodiments, such as that shown in FIG. 6B, upon one or more maximization iterations for the reference model, the system finds that the updated $T_S^{UB}$ is smaller than $T_O$. In FIG. 6B, such a situation is reached at the iteration marked 651. At iteration 651, the index for the reference model (graph 660) reaches a value 664. The difference between value 664 (the updated index value for the reference model) and value 626 (the maximum index value for the alternative model) results in an updated $T_S^{UB}$ shown as vertical bar 682. In this case, updated $T_S^{UB}$ 682 is smaller than observed index difference 254.

Upon determining that the updated $T_S^{UB}$ is smaller than $T_O$ (decision block 474: Yes), the system ends the maximization iterations for the reference model. Such a situation is shown in FIG. 6B, in which the system ends updating graph 660 beyond iteration 651. Further, the system conclusively decides that for this simulation iteration, the incident counter should not be incremented.

Similar to the embodiments depicted in FIGS. 5A and 5B, the embodiments shown in FIGS. 6A and 6B are examples of early stop simulations. In these embodiments, for one set of simulated data, the system stops the maximization iterations for the reference model before finding its maximum. Instead, the system makes a conclusive decision that the incident counter should not be incremented based on results of an earlier iteration, i.e., at the first iteration (FIG. 6A) or at some subsequent iteration before the last maximization iteration for the reference model (FIG. 6B).

In some embodiments, the $T_S^{UB}$ remains larger than or equal to $T_O$ even when the system reaches the last maximization iteration for the reference model (decision block 476: Yes). In such a situation, the system exits the maximization iteration and increments the incident counter in block 478. In some embodiments, such a situation occurs when the index function for the reference models, such as graph 660 in FIG. 6B, reaches its maximum. In this case, the last updated index value for the reference model is the maximum simulated index for the reference model, and the last updated $T_S^{UB}$ is the simulated index difference $T_s^i$. In such a situation, the system can conclusively decide that the simulated index difference $T_s^i$ is larger than or equal to the observed index difference $T_O$. Based on this conclusion, the system increments the incident counter for the present simulation data.

In various embodiments, at the start of each simulation iteration the system selects one of the reference and alternative models as the first model to maximize and the other one as the second model. In some embodiments, the system makes this selection based on the results of previous simulation iterations. In particular, in some embodiments, the system uses a biased random selection based on those results. In some embodiments, the system first determines a frequency value, which is the ratio of times in the previous iterations in which the simulated index difference $T_s^i$ was found to be larger than or equal to the observed index difference $T_O$. Such iterations indicate the cases in which comparing the observed index difference with the lower boundary for the simulated index difference requires less or at most the same number of maximization iterations as compared to comparing it with the upper boundary for the simulate index difference. The system thus determines the probability of selecting the reference model as the first model based the frequency value, with a higher probability for a larger frequency value.

In some embodiments, the system generates a random number with a Bernoulli distribution for which the success probability is the frequency value. Then, the system selects the reference model as the first model if the random number is one, and otherwise selects the alternative model. According to some embodiments, if the system selects the reference model as the first model, the system performs the process of FIG. 4B; and if the system selects the alternative model as the first model, the system performs the process of FIG. 4C.

The following is an exemplary high level software code that may be executed by a computer to implement the comparison according to some embodiments.

```
1:  Derive φ̂₁ₒ, φ̂₂ₒ and T_O
2:  For i = 1 then to n_sim do
3:    Simulate data y_sim under H₀: y_sim
        is drawn from the density P(y |φ̂₁ₒ, M₁)
4:    if i = 1 then
5:      f = 0.5
6:    else
7:      
            f = (Σ_{r=1}^{i-1} I(T_S^{(r)} ≥ T_O)) / (i - 1)
8:    end if
9:    Generate u ~Bernoulli (f)
10:   if u = 1 then
11:     T_S^{(i)LB} = 2{logP(y_sim|φ̂₂ₒ, M₂) − max_{φ₁} logP(Y_sim|φ₁, M₁)}
12:     if T_S^{(i)LB} ≥ T_O then
13:       Record that T_S^{(i)LB} ≥ T_O for iteration i by setting I (T_S^{(i)} ≥ T_O) = 1
14:     else
15:       T_S^{(i)} = T_S^{(i)LB} + 2{max_{φ₂} logP(y_sim|φ₂, M₂) − logP(y_sim|φ̂₂ₒ, M₂)}
16:       If T_S^{(i)} ≥ T_O then set I(T_S^{(i)} ≥ T_O) = 1
          otherwise set I(T_S^{(i)} ≥ T_O) = 0
17:     end if
18:   else if u = 0 then
19:     T_S^{(i)UB} = 2{max_{φ₂} logP(y_sim|φ₂, M₂) − logP(y_sim|φ̂₁ₒ, M₁)}
20:     if T_S^{(i)UB} < T_O then
21:       Record that T_S^{(i)} < T_O for iteration i by setting I (T_S^{(i)} ≥ T_O) = 0
22:     else
23:       T_S^{(i)} = T_S^{(i)UB} + 2{y_sim|φ̂₁ₒ, M₁) − max_{φ₁} logP(y_sim|φ₁, M₁)}
24:       If T_S^{(i)} ≥ T_O then set I(T_S^{(i)} ≥ T_O) = 1 otherwise I(t_s^{(i)} ≥ t_o) = 0
25:     end if
26:   end if
27: end for
28:   
         P(T_O) ≜ (1 + Σ_{i=1}^{n_sim} I(T_S^{(i)} ≥ T_O)) / (1 + n_sim)
```

At line 1 of the code, the system derives the observed fits parameters φ̂₁ₒ and φ̂₂ₒ and the observed index difference $T_O$. In some embodiments, the system derives these observed values using equations such as Equations (3c), (3d), and (4). A line 2, the system starts the simulation iterations. The simulation iteration loop starts at line 2 and ends at line 27.

At line 3, the system generates a set of simulated data under the null hypothesis (H0). At lines 4-8, the system calculates the frequency value, f. For the first iteration, the frequency value is 0.5, and otherwise it is the ratio of prior simulations in which the simulated index difference was larger than or equal to the observed index difference. At line 9, the system generates a random number based on a Bernoulli distribution with a probability of f. If the random number is 1, the system performs a first block of code at lines 11-17, in which the system finds the lower boundary for the simulated index difference. If, on the other hand, the random number is 0, the system performs a second block of code at lines 19-25, in which the system finds the upper boundary for the simulated index difference.

In the first block of code, at line 11, the system finds the initial value of $T_S^{(i)LB}$, the lower boundary for the simulated index difference for this simulation iteration indexed i. The system finds this initial value of $T_S^{(i)LB}$ by finding the maximum simulated index for the reference model (i.e., finding $\max_{\phi_1} \log P(y_{sim}|\phi_1, M_1)$) and subtracting that value from the initial simulated index for the alternative model (log $P(y_{sim}|\hat{\phi}_{2o}, M_2)$).

At line 12, the system compares the initial value of the lower boundary with the observed index difference $T_O$. If the lower boundary is larger than or equal to the observed index difference, at line 13 the system sets the incident recorder I ($T_S^{(i)} \geq T_O$) to one for this simulation set.

If, on the other hand, the lower boundary is smaller than the observed index difference, the system derives the simulated index difference $T_S^{(i)}$ at line 15. In particular, at line 15 the system finds the maximum simulated index for the alternative model ($\max_{\phi_2} \log P(y_{sim}|\phi_2, M_2)$) and then, through the calculation at line 15, replaces in the previously derived $T_S^{(i)LB}$ the initial simulated index for the alternative model (log $P(y_{sim}|\hat{\phi}_{2o}, M_2)$) with the newly derived maximum simulated index for the alternative model. In some embodiments, the system does complete the maximization for the alternative model and instead stops that maximization early and before reaching the maximum, in the manner explained, for example, in relation to FIG. 5B.

At line 16, the system checks whether the simulated index difference is larger than or equal to the observed index difference ($T_S^{(i)} \geq T_O$). If the answer is yes, the system records the incident by setting the incident recorder I ($T_S^{(i)} \geq T_O$) to one, and otherwise by setting it to zero.

In the second block of code, at line 19, the system finds the initial value of $T_S^{(i)UB}$, the upper boundary for the simulated index difference for this simulation. The system finds this initial value of $T_S^{(i)uB}$ by finding the maximum simulated index for the alternative model (i.e., finding $\max_{\phi_2} \log P(y_{sim}|\phi_2, M_2)$) and subtracting from it the initial simulated index for the reference model (log $P(y_{sim}|\hat{\phi}_{1o}, M_1)$).

At line 20, the system compares the initial value of the upper boundary with the observed index difference $T_O$. If the upper boundary is smaller than the observed index difference, at line 21 the system sets the incident recorder I ($T_S^{(i)} \geq T_O$) to zero for this simulation set.

If, on the other hand, the upper boundary is not smaller than the observed index difference, the system derives the simulated index difference $T_S^{(i)}$ at line 23. In particular, at line 23 the system finds the maximum simulated index for the reference model ($\max_{\phi_1} \log P(y_{sim}|\phi_1, M_1)$) and then, through the calculation at line 23, replaces in the previously derived $T_S^{(i)UB}$ the initial simulated index for the reference model (log $P(y_{sim}|\hat{\phi}_{2o}, M_2)$) with the newly derived maximum simulated index for the reference model. In some embodiments, the system does complete the maximization for the reference model and instead stops that maximization early and before reaching the maximum, in the manner explained, for example, in relation to FIG. 6B.

At line 24, the system checks whether the simulated index difference is larger than or equal to the observed index difference ($T_S^{(i)} \geq T$). If the answer is yes, the system records the incident by setting I ($T_S^{(i)} \geq T$) to one, and otherwise by setting it to zero.

At line 28, the system derives the p-value for the observed index difference $P(T_O)$ using Equation (7).

Figure 7:
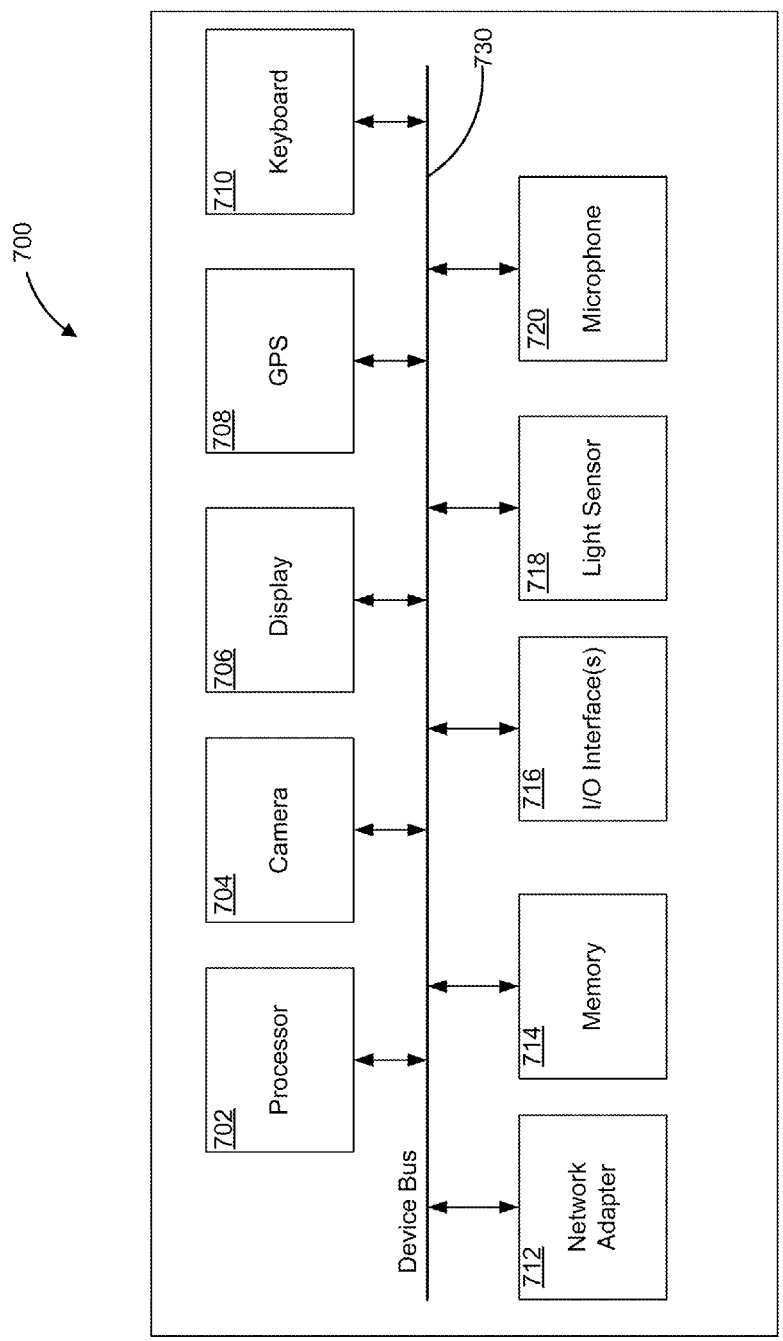
FIG. 7 is a block diagram of an exemplary computing system according to some embodiment.

The disclosed systems or modules may be implemented via one or more computing devices or systems. FIG. 7 is a block diagram of an exemplary computing system 700 according to some embodiment. System 700 includes a processor 702, a display 706, a memory 714, a keyboard 710, and other I/O interfaces 716, and a network adapter 712. Further, system 700 includes one or more sensors, such as a camera 704, a global positioning service (GPS) receiver 708, a light sensor 718, and a microphone 720. In various embodiments, the aforementioned components are comprised in a single device. Some or all of the components may communicate, for example, via bus 730. Some components may be external to the device and communicate via a wired or wireless connection.

In various embodiments, processor 702 may be a microprocessor or a central processor unit (CPU) performing various methods in accordance to the embodiment. Memory 714 may include a computer hard disk, a random access memory (RAM), a removable storage, or a remote computer storage. In various embodiments, memory 714 stores various software programs executed by processor 702. Network adapter 712 enables system 700 to exchange information with external networks. In various embodiments, network adapter 712 includes a wireless wide area network (WWAN) adapter, or a local area network (LAN) adapter. I/O interfaces 716 may include keyboard 710, or a mouse, an audio input device, a touch screen, or an infrared input interface.

In various embodiments, one or more of modules disclosed in this disclosure are implemented via one or more processors executing software programs for performing the functionality of the corresponding modules. In some embodiments, one or more of the disclosed modules are implemented via one or more hardware modules executing firmware for performing the functionality of the corresponding modules. In various embodiments, one or more of the disclosed modules include storage media for storing data used by the module, or software or firmware programs executed by the module. In various embodiments, one or more of the disclosed modules or disclosed storage media are internal or external to the disclosed systems. In some embodiments, one or more of the disclosed modules or storage media are implemented via a computing "cloud", to which the disclosed system connects via an internet and accordingly uses the external module or storage medium. In some embodiments, the disclosed storage media for storing information include non-transitory computer-readable media, such as a CD-ROM, a computer storage, e.g., a hard disk, or a flash memory. Further, in various embodiments, one or more of the storage media are non-transitory computer-readable media storing information or software programs executed by various modules or implementing various methods or flow charts disclosed herein.

In various embodiments, an I/O module is configured to receive inputs and to provide outputs. In some embodiments, the I/O module is an interface for receiving and sending data to a user or to another system. In various embodiments, the I/O module includes an input interface and an output interface. The input interface is configured to receive data, such as commands, and the output interface is configured to output information such as p-value or comparison results. In some embodiments, the I/O module includes one or more of an internet interface, a wireless interface, a data reader, a mouse, a keyboard, a display, a speaker, a touch screen, or a printer.

The foregoing description of the invention, along with its associated embodiments, has been presented for purposes of illustration only. It is not exhaustive and does not limit the invention to the precise form disclosed. Those skilled in the art will appreciate from the foregoing description that modifications and variations are possible in light of the above teachings or may be acquired from practicing the invention. For example, the steps described need not be performed in the same sequence discussed or with the same degree of separation. Likewise various steps may be omitted, repeated, or combined, as necessary, to achieve the same or similar objectives. Similarly, the systems described need not necessarily include all parts described in the embodiments, and may also include other parts not described in the embodiments. Accordingly, the invention is not limited to the above-described embodiments, but instead is defined by the appended claims in light of their full scope of equivalents.

The invention claimed is:

1. A method for model selection, the method comprising:
   selecting, by one or more processors, a reference model as a possible description of a set of observed data, wherein the reference model includes a reference set of parameters;
   selecting, by the one or more processors, an alternative model as another possible description of the set of observed data, wherein the alternative model includes an alternative set of parameters;
   storing, by the one or more processors, an index function for measuring fit of models to data;
   calculating, by the one or more processors, an observed index difference based on a difference in the index function for fitting the reference model to the set of observed data and for fitting the alternative model to the set of observed data;
   determining, by the one or more processors, a simulated p-value using an comparison system that determines a threshold-fit simulated index for a first model and, while an early stop condition remains unsatisfied, iteratively compares the observed index difference to a boundary for a simulated index difference, the boundary for the simulated index difference based on a simulated index for a second model, determination of the simulated p-value comprising:
   generating, by the one or more processors, a set of simulated data;
   selecting, by the one or more processors, the first model and the second model, wherein the first model is one of the reference model and the alternative model and the second model is the other one of the reference model and the alternative model;
   performing, by the one or more processors, an operation based on the set of simulated data, wherein the operation includes:
   performing a simulated threshold-fitting for the first model by the one or more processors, wherein the simulated threshold-fitting for the first model includes varying a set of parameters for the first model for fitting the first model to the set of simulated data and deriving the threshold-fit simulated index for the first model as a value of the index function for the first model that satisfies a threshold criterion;
   deriving an initial simulated index for the second model as an initial value of the index function for fitting the second model to the set of simulated data; and
   deriving an initial boundary for the simulated index difference, wherein deriving the initial boundary for the simulated index difference includes calculating a difference between the threshold-fit simulated index for the first model and the initial simulated index for the second model;
   determining, by the one or more processors, based on a comparison of the initial boundary for the simulated index difference and the observed index difference, whether to update a counter used in calculating the simulated p-value; and
   selecting, by the one or more processors based on the simulated p-value, one of the reference model and the alternative model for modeling the set of observed data.

2. The method of claim 1, wherein the simulated threshold-fitting includes a first maximization, and wherein the first maximization includes deriving the threshold-fit simulated index for the first model as a maximum simulated index for the first model by varying the set of parameters for the first model and maximizing the index function for fitting the first model to the set of simulated data.

3. The method of claim 1, further comprising storing observed fit parameters for the reference model based on maximizing the index function for fitting the reference model to the set of observed data, and storing observed fit parameters for the alternative model based on maximizing the index function for fitting the alternative model to the set of observed data.

4. The method of claim 3, wherein deriving the initial simulated index for the second model includes setting a set of parameters for the second model to the observed fit parameters for the second model and deriving the index function for fitting the second model to the set of simulated data.

5. The method of claim 1, wherein the operation further comprises:
deriving an updated boundary for the simulated index difference, wherein deriving the updated boundary for the simulated index difference includes deriving an updated simulated index for the second model as an updated value of the index function for fitting the second model to the set of simulated data and calculating a difference between the threshold-fit simulated index for the first model and the updated simulated index for the second model;
and wherein the method further comprises determining, based on a comparison of the updated boundary for the simulated index difference and the observed index difference, whether to update the counter.

6. The method of claim 1, wherein the first model is the reference model and the second model is the alternative model, and wherein the initial boundary for the simulated index difference is an initial lower boundary for the simulated index difference, and wherein the determining whether to update the counter includes increasing the counter if the initial lower boundary for the simulated index difference is larger than or equal to the observed index difference, and wherein the early stop condition is satisfied when the initial lower boundary for the simulated index difference is larger than or equal to the observed index difference.

7. The method of claim 6, wherein the operation further comprises:
determining that the initial lower boundary for the simulated index difference is smaller than the observed index difference; and
deriving an updated lower boundary for the simulated index difference, wherein deriving the updated lower boundary for the simulated index difference includes deriving an updated simulated index for the alternative model as an updated value of the index function for fitting the alternative model to the set of simulated data and subtracting the threshold-fit simulated index for the reference model from the updated simulated index for the alternative model;
and wherein the method further comprises increasing the counter if the updated lower boundary for the simulated index difference is larger than or equal to the observed index difference, and wherein the early stop condition is satisfied when the updated lower boundary for the simulated index difference is larger than or equal to the observed index difference.

8. The method of claim 7, wherein deriving the updated simulated index for the alternative model includes deriving a maximum simulated index for the alternative model via maximizing the index function for fitting the alternative model to the set of simulated data, wherein deriving the updated lower boundary for the simulated index difference includes deriving the simulated index difference by subtracting the threshold-fit simulated index for the reference model from the maximum simulated index for the alternative model, and wherein the method further comprises:
increasing the counter if the simulated index difference is larger than or equal to the observed index difference; and
determining to leave the counter unchanged if the simulated index difference is smaller than the observed index difference.

9. The method of claim 1, wherein the first model is the alternative model and the second model is the reference model, and wherein the initial boundary for the simulated index difference is an initial upper boundary for the simulated index difference, and wherein the determining whether to update the counter includes determining to leave the counter unchanged if the initial upper boundary for the simulated index difference is smaller than the observed index difference, and wherein the early stop condition is satisfied when the initial upper boundary for the simulated index difference is smaller than the observed index difference.

10. The method of claim 9, wherein the operation further comprises:
determining that the initial upper boundary for the simulated index difference is not smaller than the observed index difference; and
deriving an updated upper boundary for the simulated index difference, wherein deriving the updated upper boundary for the simulated index difference includes deriving an updated simulated index for the reference model as an updated value of the index function for fitting the reference model to the set of simulated data and subtracting the updated simulated index for the reference model from the threshold-fit simulated index for the alternative model;
and wherein the method further comprises determining to leave the counter unchanged if the updated upper boundary for the simulated index difference is smaller than the observed index difference, and wherein the early stop condition is satisfied when the updated upper boundary for the simulated index difference is smaller than the observed index difference.

11. The method of claim 10, wherein deriving the updated simulated index for the reference model includes deriving a maximum simulated index for the reference model via maximizing the index function for fitting the reference model to the set of simulated data, wherein deriving the updated upper boundary for the simulated index difference includes deriving the simulated index difference by subtracting the maximum simulated index for the reference model from the threshold-fit simulated index for the alternative model, and wherein the method further comprises:
increasing the counter if the simulated index difference is larger than or equal to the observed index difference; and
determining to leave the counter unchanged if the simulated index difference is smaller than the observed index difference.

29

12. The method of claim 1, wherein each iteration of the iterative comparison comprises generating an additional set of simulated data.

13. The method of claim 12, wherein each iteration of the iterative comparison further comprises stochastically selecting the reference model or the alternative model as the first model.

14. The method of claim 13, wherein the stochastic selection depends on an outcome of one or more previous iterations of the iterative comparison.

15. The method of claim 14, wherein each iteration of the iterative comparison further includes:
setting a weight value to 0.5 if an iteration of the iterative comparison is a first iteration of the iterative comparison;
otherwise calculating the weight value as a ratio of previous iterations in which the counter was decided to be increased; and
creating a random variable for which a probability of being one is the weight value; and
setting the first model to be the reference model if the random variable is one, otherwise setting the first model to be the alternative model.

16. The method of claim 12, wherein iterations of the iterative comparison are performed in parallel.

17. The method of claim 1, wherein the index function is a logarithm of a density function.

18. The method of claim 1, wherein the selection of at least one of the reference model as the possible description of the set of observed data and the alternative model as another possible description of the set of observed data is based on information received from a user.

19. A system for model selection, the system comprising:
a comparison system, including one or more processors, for determining a simulated p-value that determines a threshold-fit simulated index for a first model and, while an early stop condition remains unsatisfied, iteratively compares an observed index difference to a boundary for a simulated index difference, the boundary for the simulated index difference based on a simulated index for a second model, the comparison system comprising:
an analyzer that:
selects a reference model as a possible description of a set of observed data, wherein the reference model includes a reference set of parameters,
selects an alternative model as another possible description of the set of observed data, wherein the alternative model includes an alternative set of parameters,
stores an index function for measuring fit of models to data,
calculates the observed index difference based on a difference in the index function for fitting the reference model to the set of observed data and for fitting the alternative model to the set of observed data, and
selects the first model and the second model, wherein the first model is one of the reference model and the alternative model and the second model is the other one of the reference model and the alternative model,
a simulator that generates a set of simulated data;
a first maximizer that performs an operation based on the set of simulated data, wherein the operation includes performing a simulated threshold-fitting for the first model by the one or more processors,

30 wherein the simulated threshold-fitting for the first model includes varying a set of parameters for the first model for fitting the first model to the set of simulated data and deriving the threshold-fit simulated index for the first model as a value of the index function for the first model that satisfies a threshold criterion; and
a second maximizer that derives an initial simulated index for the second model as an initial value of the index function for fitting the second model to the set of simulated data; and
wherein the analyzer further:
derives an initial boundary for the simulated index difference, wherein deriving the initial boundary for the simulated index difference includes calculating a difference between the threshold-fit simulated index for the first model and the initial simulated index for the second model;
determines, based on a comparison of the initial boundary for the simulated index difference and the observed index difference, whether to update a counter used in calculating the simulated p-value; and
selects, based on the simulated p-value, one of the reference model and the alternative model for modeling the set of observed data.

20. The system of claim 19, wherein the analyzer selects at least one of the reference model as the possible description of the set of observed data and the alternative model as another possible description of the set of observed data based on information received from a user.

21. A non-transitory computer-readable medium storing a computer program, wherein the computer program, when executed by one or more processors, causes the one or more processors to execute a method for model selection, the method comprising:
selecting a reference model as a possible description of a set of observed data, wherein the reference model includes a reference set of parameters;
selecting an alternative model as another possible description of the set of observed data, wherein the alternative model includes an alternative set of parameters;
storing an index function for measuring fit of models to data;
calculating an observed index difference based on a difference in the index function for fitting the reference model to the set of observed data and for fitting the alternative model to the set of observed data;
determining a simulated p-value using an comparison system that determines a threshold-fit simulated index for a first model and, while an early stop condition remains unsatisfied, iteratively compares the observed index difference to a boundary for a simulated index difference, the boundary for the simulated index difference based on a simulated index for a second model, determination of the simulated p-value comprising:
generating a set of simulated data;
selecting the first model and the second model, wherein the first model is one of the reference model and the alternative model and the second model is the other one of the reference model and the alternative model;
performing, by the one or more processors, an operation based on the set of simulated data, wherein the operation includes:
performing a simulated threshold-fitting for the first model by the one or more processors, wherein the simulated threshold-fitting for the first model includes varying a set of parameters for the first model for fitting the first model to the set of simulated data and deriving the threshold-fit simulated index for the first model as a value of the index function for the first model that satisfies a threshold criterion;

deriving an initial simulated index for the second model as an initial value of the index function for fitting the second model to the set of simulated data; and deriving an initial boundary for the simulated index difference, wherein deriving the initial boundary for the simulated index difference includes calculating a difference between the threshold-fit simulated index for the first model and the initial simulated index for the second model;

determining, based on a comparison of the initial boundary for the simulated index difference and the observed index difference, whether to update a counter used in calculating the simulated p-value; and selecting, based on the simulated p-value, one of the reference model and the alternative model for modeling the set of observed data.

22. The medium of claim 21, wherein the selection of at least one of the reference model as the possible description of the set of observed data and the alternative model as another possible description of the set of observed data is based on information received from a user.

\* \* \* \* \*